(12) United States Patent
Erdtmann

(10) Patent No.: US 9,482,607 B2
(45) Date of Patent: *Nov. 1, 2016

(54) METHODS OF SMOKE DETECTING USING TWO DIFFERENT WAVELENGTHS OF LIGHT AND AMBIENT LIGHT DETECTION FOR MEASUREMENT CORRECTION

(71) Applicant: Matthew Erdtmann, Londonderry, NH (US)

(72) Inventor: Matthew Erdtmann, Londonderry, NH (US)

(73) Assignee: Valor Fire Safety, LLC, Londonderry, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/821,155

(22) Filed: Aug. 7, 2015

(65) Prior Publication Data

US 2015/0346086 A1   Dec. 3, 2015

Related U.S. Application Data

(63) Continuation of application No. 14/522,971, filed on Oct. 24, 2014, now Pat. No. 9,140,646, which is a continuation-in-part of application No. 14/067,431, filed on Oct. 30, 2013, now Pat. No. 8,907,802, which (Continued)

(51) Int. Cl.
| | |
|---|---|
| *G08B 21/00* | (2006.01) |
| *G01N 21/27* | (2006.01) |
| *G01N 21/53* | (2006.01) |
| *G08B 17/107* | (2006.01) |
| *G08B 29/18* | (2006.01) |

(52) U.S. Cl.
CPC ............ *G01N 21/274* (2013.01); *G01N 21/53* (2013.01); *G08B 17/107* (2013.01); *G01N 2201/062* (2013.01); *G01N 2201/12746* (2013.01); *G08B 29/185* (2013.01)

(58) Field of Classification Search
CPC ............................. G08B 17/103; G01N 21/53
USPC ..................... 340/515, 628, 629, 630, 693.5; 250/574, 575; 356/437, 438, 439
See application file for complete search history.

(56) References Cited

U.S. PATENT DOCUMENTS

| | | |
|---|---|---|
| 2,654,082 A | 9/1953 | Cahusac et al. |
| 2,935,135 A | 5/1960 | Grant, Jr. |

(Continued)

FOREIGN PATENT DOCUMENTS

| | | |
|---|---|---|
| CA | 2318110 A1 | 7/1999 |
| EP | 1975896 A2 | 10/2008 |

(Continued)

OTHER PUBLICATIONS

"Economical Smoke Detector Avoids False Alarms" Electronic Design, http://electronicdesign.com/analog/economical-smoke-detector-avoids-false-alarms. Sep. 19, 2011.

(Continued)

*Primary Examiner* — Jeffery Hofsass
(74) *Attorney, Agent, or Firm* — Morgan, Lewis & Bockius LLP

(57) ABSTRACT

In accordance with certain embodiments, a smoke detector determines the presence of smoke particles outside its housing based on measurements of light detected at different wavelengths and corrected based on an ambient light level.

24 Claims, 10 Drawing Sheets

Related U.S. Application Data is a continuation-in-part of application No. 13/799,816, filed on Mar. 13, 2013, now Pat. No. 8,947,243, said application No. 14/067,431 is a continuation-in-part of application No. 13/799,826, filed on Mar. 13, 2013, now Pat. No. 8,952,821, and a continuation-in-part of application No. 13/800,071, filed on Mar. 13, 2013, now Pat. No. 8,947,244.

(60) Provisional application No. 61/639,935, filed on Apr. 29, 2012.

(56) References Cited

U.S. PATENT DOCUMENTS

| | | |
|---|---|---|
| 3,231,748 A | 1/1966 | Haessler et al. |
| 3,409,885 A | 11/1968 | Hall |
| 3,874,795 A | 4/1975 | Packham et al. |
| 3,882,477 A | 5/1975 | Mueller |
| 3,930,247 A | 12/1975 | Hurd |
| 3,938,115 A | 2/1976 | Jacoby |
| 4,058,253 A | 11/1977 | Munk et al. |
| 4,155,653 A | 5/1979 | San Miguel et al. |
| 4,166,698 A | 9/1979 | Steele |
| 4,185,278 A | 1/1980 | Lintelmann et al. |
| 4,206,366 A | 6/1980 | Marsocci et al. |
| 4,292,513 A | 9/1981 | Simmons et al. |
| 4,300,133 A | 11/1981 | Solomon |
| 4,547,673 A | 10/1985 | Larsen et al. |
| 4,615,224 A | 10/1986 | Smith et al. |
| 4,665,311 A | 5/1987 | Cole |
| 4,714,347 A | 12/1987 | Cole |
| 4,827,247 A | 5/1989 | Giffone |
| 5,231,378 A | 7/1993 | Dennis et al. |
| 5,352,901 A | 10/1994 | Poorman |
| 5,410,299 A | 4/1995 | Hard |
| 5,818,326 A | 10/1998 | Winterble et al. |
| 5,917,417 A | 6/1999 | Girling et al. |
| 5,966,077 A | 10/1999 | Wong |
| 6,111,511 A | 8/2000 | Sivathanu et al. |
| 6,222,455 B1 | 4/2001 | Kaiser |
| 6,285,291 B1 | 9/2001 | Knox et al. |
| 6,426,703 B1 | 7/2002 | Johnston et al. |
| 6,515,589 B2 | 2/2003 | Schneider et al. |
| 6,741,181 B2 | 5/2004 | Skaggs |
| 6,778,091 B2 | 8/2004 | Qualey, III et al. |
| 6,788,197 B1 | 9/2004 | Thuillard et al. |
| 6,914,535 B2 | 7/2005 | Matsukuma et al. |
| 6,967,582 B2 | 11/2005 | Tice et al. |
| 7,005,999 B2 | 2/2006 | Salzhauer et al. |
| 7,034,702 B2 | 4/2006 | Thomas et al. |
| 7,062,953 B2 | 6/2006 | Yamano et al. |
| 7,068,177 B2 | 6/2006 | Tice |
| 7,075,646 B2 | 7/2006 | Cole |
| 7,142,105 B2 | 11/2006 | Chen |
| 7,233,253 B2 | 6/2007 | Qualey, III |
| 7,327,247 B2 | 2/2008 | Tice |
| 7,474,227 B2 | 1/2009 | Qualey, III |
| 7,483,139 B2 | 1/2009 | Powell |
| 7,503,230 B2 | 3/2009 | Bell et al. |
| 7,551,096 B2 | 6/2009 | Tice |
| 7,602,304 B2 | 10/2009 | Tice |
| 7,607,798 B2 | 10/2009 | Panotopoulos |
| 7,642,924 B2 | 1/2010 | Andres et al. |
| 7,669,457 B2 | 3/2010 | Griffith et al. |
| 7,746,239 B2 | 6/2010 | Nagashima |
| 7,769,204 B2 | 8/2010 | Privalov |
| 7,817,049 B2 | 10/2010 | Muller et al. |
| 7,821,412 B2 | 10/2010 | Fink |
| 7,847,700 B2 | 12/2010 | Conforti |
| 7,884,731 B2 | 2/2011 | Mizuo |
| 7,928,854 B2 | 4/2011 | Martino |
| 7,940,190 B2 | 5/2011 | Penney |
| 7,948,627 B2 | 5/2011 | Iguchi et al. |
| 7,978,087 B2 | 7/2011 | Siber et al. |
| 8,077,046 B1 | 12/2011 | Wong |
| 8,089,374 B2 | 1/2012 | Mayer et al. |
| 8,106,785 B2 | 1/2012 | Yokota |
| 8,199,029 B2 | 6/2012 | Bell et al. |
| 8,284,065 B2 | 10/2012 | Gonzales |
| 8,907,802 B2 | 12/2014 | Erdtmann |
| 8,947,243 B2 | 2/2015 | Erdtmann |
| 8,947,244 B2 | 2/2015 | Erdtmann |
| 8,952,821 B2 | 2/2015 | Erdtmann |
| 2002/0080040 A1 | 6/2002 | Schneider et al. |
| 2004/0012951 A1 | 1/2004 | Pylkki et al. |
| 2004/0021576 A1 | 2/2004 | Scott et al. |
| 2005/0019947 A1 | 1/2005 | Ito et al. |
| 2006/0181407 A1 | 8/2006 | Tice |
| 2006/0261967 A1 | 11/2006 | Marman et al. |
| 2007/0168140 A1 | 7/2007 | Knox |
| 2008/0246623 A1 | 10/2008 | Nagashima |
| 2009/0241697 A1 | 10/2009 | Kato et al. |
| 2009/0256714 A1 | 10/2009 | Loepfe et al. |
| 2010/0118303 A1 | 5/2010 | Nagashima |
| 2010/0238036 A1 | 9/2010 | Holcombe |
| 2011/0037971 A1 | 2/2011 | Loepfe et al. |
| 2011/0057805 A1 | 3/2011 | Loepfe et al. |
| 2011/0108748 A1 | 5/2011 | Vollenweider |
| 2011/0188039 A1 | 8/2011 | Aoyama |
| 2011/0221889 A1 | 9/2011 | Knox et al. |
| 2011/0255091 A1 | 10/2011 | Aebersold et al. |
| 2012/0050051 A1 | 3/2012 | Clossen-Von Lanken Schulz |
| 2012/0140231 A1 | 6/2012 | Knox et al. |
| 2013/0208281 A1 | 8/2013 | Masumoto et al. |
| 2013/0286391 A1 | 10/2013 | Erdtmann |
| 2013/0286392 A1 | 10/2013 | Erdtmann |
| 2013/0286393 A1 | 10/2013 | Erdtmann |
| 2014/0333928 A1 | 11/2014 | Erdtmann |
| 2015/0102934 A1 | 4/2015 | Erdtmann |
| 2015/0102935 A1 | 4/2015 | Erdtmann |
| 2015/0103346 A1 | 4/2015 | Erdtmann |
| 2015/0116711 A1 | 4/2015 | Erdtmann |

FOREIGN PATENT DOCUMENTS

| | | |
|---|---|---|
| EP | 2000952 A2 | 12/2008 |
| EP | 2141484 A1 | 1/2010 |
| EP | 2273466 A1 | 1/2011 |
| EP | 2463837 A1 | 6/2012 |
| JP | 03250395 | 11/1991 |
| JP | 04259845 | 9/1992 |
| JP | 11023458 | 1/1999 |
| JP | 2004-220155 | 8/2004 |
| JP | 2011203889 A | 10/2011 |
| JP | 2011203890 A | 10/2011 |
| JP | 2011203892 A | 10/2011 |
| KR | 10-1098969 | 12/2011 |
| RU | 2438185 C1 | 12/2011 |
| TW | 201027466 A | 7/2010 |
| WO | WO-9219955 A1 | 11/1992 |
| WO | WO-0007161 A1 | 2/2000 |
| WO | WO-2011098773 A1 | 8/2011 |
| WO | WO-2011106840 A1 | 9/2011 |
| WO | WO2013165713 | 11/2013 |

OTHER PUBLICATIONS

International Search Report and Written Opinion mailed Aug. 23, 2013 for corresponding International Application No. PCT/US2013/037522 (28 pages).

PCT International Patent Application No. PCT/US2013/037522, International Search Report on Patentability mailed Nov. 13, 2014, 25 pages.

PCT International Patent Application No. PCT/US2014/62560, International Search Report and Written Opinion mailed Feb. 6, 2015, 49 pages.

METHODS OF SMOKE DETECTING USING TWO DIFFERENT WAVELENGTHS OF LIGHT AND AMBIENT LIGHT DETECTION FOR MEASUREMENT CORRECTION

RELATED APPLICATIONS

This application is a continuation of U.S. patent application Ser. No. 14/522,971, filed on Oct. 24, 2014, which a continuation-in-part of U.S. patent application Ser. No. 14/067,431, filed Oct. 30, 2013, which is (a) a continuation-in-part of U.S. patent application Ser. No. 13/799,816, filed Mar. 13, 2013, which claims the benefit of and priority to U.S. Provisional Patent Application No. 61/639,935, filed Apr. 29, 2012, (b) a continuation-in-part of U.S. patent application Ser. No. 13/799,826, filed Mar. 13, 2013, which claims the benefit of and priority to U.S. Provisional Patent Application No. 61/639,935, filed Apr. 29, 2012, and (c) a continuation-in-part of U.S. patent application Ser. No. 13/800,071, filed Mar. 13, 2013, which claims the benefit of and priority to U.S. Provisional Patent Application No. 61/639,935, filed Apr. 29, 2012. The entire disclosure of each of these applications is hereby incorporated herein by reference.

FIELD OF THE INVENTION

In various embodiments, the present invention generally relates to smoke detectors and, in particular, to such detectors having external sampling volumes.

BACKGROUND

A smoke detector with an external sampling volume operates by emitting light outside its housing and detecting light scattered back into the housing by smoke particles located within the sampling volume. Smoke detectors with an external sampling volume have several important benefits over conventional ionization and photoelectric smoke detectors. First, by eliminating the internal sensing chamber and the slow accumulation of smoke particles therein, the lag time between when a threshold smoke density is reached outside the detector and when the smoke detector responds is substantially eliminated. This increases the Available Safe Egress Time (ASET), the time available for occupants to safely evacuate a building before the fire renders evacuation impossible. Second, by obviating the need for the entry of smoke particles into the housing, the entirety of the smoke detector may be mounted within an opening in a ceiling or wall, such that there is minimal protrusion outward from the surface; such flush mounting of the smoke detector creates an aesthetically pleasing appearance. Third, the smoke-detecting element may be fully tested. In conventional ionization and photoelectric smoke detectors equipped with a test feature, the testing mechanism tests the electrical circuitry only, but in smoke detectors with an external sampling volume, the operation of the smoke-detecting element may be tested by inserting an object into the sampling volume.

Despite these benefits, smoke detectors with an external sampling volume have not been widely deployed. One reason is the difficulty of these smoke detectors to isolate the signal generated by the scattered light from the signal generated by ambient light, especially when there is a change in the ambient light level. Another reason is the difficulty these smoke detectors have distinguishing smoke particles from nuisance particles or other objects. The ambiguity in both cases may lead to false alarms when a nuisance source is present or a lack of response when a fire source is present.

Accordingly, there is a need for smoke detectors with an external sampling volume, and related detection techniques, which can reject the influence of ambient light and distinguish smoke particles from nuisance particles and objects.

SUMMARY

In accordance with various embodiments of the present invention, a smoke detector uses a proximity sensor (or multiple components collectively providing the functionality of a proximity sensor) to detect the presence of smoke outside the detector. The proximity sensor generally operates by emitting a beam of light and detecting any scattered or reflected signal from an object located within a specified range. The proximity sensor features at least one light detector (which is typically but not necessarily embedded in the proximity sensor), along with control circuitry and signal processing circuitry. At least one light emitter may also be embedded in the proximity sensor or may be discrete but externally driven by the proximity sensor. The smoke detector also uses an ambient-light sensor to measure and compensate for the ambient light level. The ambient-light sensor features at least one light detector (which is typically but not necessarily embedded in the ambient-light sensor), along with control circuitry and signal processing circuitry. The ambient-light sensor may be separate from the proximity sensor, or it may be part of (and even embedded within) the proximity sensor, in which case the ambient-light sensor and proximity sensor may use a common light detector. Alternative embodiments of the invention utilize a discrete light emitter and light detector in place of the proximity sensor without altering the functionality of the smoke detector. As utilized herein, a "light detector" is a discrete or embedded electronic component that registers the presence of and/or measures a property of light (e.g., luminance, wavelength, etc.) when it is illuminated by the light.

In accordance with various embodiments of the invention, the proximity sensor is disposed inside the housing of the smoke detector beneath an opening. The opening may or may not be covered by a window that is at least partially transparent to the emitted light and/or may contain an optical element such as a lens, prism, mirror, and/or grating. Most of the emitted beam passes through the opening to the environment outside the smoke detector. The region outside the smoke detector but within the specified range of the proximity sensor (or other discrete components described herein) is defined herein as the "external sampling volume." If smoke or an obstruction enters the external sampling volume, the signal generated by the proximity sensor will increase. In the case of smoke, the increase in signal arises from scattering of the emitted beam by the smoke particles. In the case of an obstruction, the increase in signal arises from the reflection of the emitted beam off of the obstruction. Because the proximity sensor is optically exposed to the outside environment via the opening, the window, and/or the optical element), its signal may also be increased or decreased by ambient light incident upon the proximity sensor. Ambient light, as utilized herein, is any light that enters the external sampling volume or the housing that did not originate from a light emitter inside or associated with the smoke detector. Example ambient light sources include sunlight or light from incandescent, fluorescent, halogen, or LED light bulbs.

An evaluation circuit may periodically or continuously analyze the signal to determine whether an obstruction, smoke, or system fault is present. Since reflection by an obstruction typically produces a distinctly stronger signal than scattering by smoke particles, an obstruction threshold is typically set higher than the maximum possible signal generated by smoke scattering. If the signal exceeds the obstruction threshold for a pre-determined amount of time, an obstruction alarm may be activated. This pre-determined delay typically eliminates unwanted alarms from fleeting events such as an insect passing through the external sampling volume.

The smoke threshold is generally set lower than the obstruction threshold but higher than the background signal, and the smoke threshold may correspond to the signal generated for a given smoke density outside the detector. If additional sensors are incorporated in the smoke detector, such as gas or heat sensors, the smoke threshold may be decreased with increasing signal from these sensors, as the signal from the additional sensor(s) may provide faster activation and greater discrimination from nuisance sources (i.e., false alarms). An advantage of embodiments of the present invention is that the proximity sensor (or equivalent component(s)) directly measures the smoke density outside the smoke detector, which substantially reduces the lag time compared to a conventional ionization or photoelectric smoke detector.

The operation of the smoke detector may be manually tested by inserting an object, such as a hand or broom handle, into the external sampling volume to activate the obstruction alarm after a pre-determined delay has elapsed. Likewise, inserting an object into the external sampling volume while an alarm is activated may temporarily silence the alarm.

Embodiments of the invention also distinguish between smoke particles and nuisance particles based at least in part on specific interactions between such particles and multiple different wavelengths of light. (As utilized herein, "nuisance particles" broadly refers to vapors or airborne particulates not originating from a fire and that typically have average diameters larger (e.g., at least ten times larger and/or at least one micron in diameter) than typical smoke particles. Non-limiting examples of nuisance particles are steam, cooking aerosols (e.g., vegetable oil, toast, hamburger, bacon, etc.), powder, and dust (e.g., cement dust).) Because nuisance particles typically are larger than smoke particles, they will tend to scatter light of various wavelengths differently. Thus, the scattering behavior over multiple wavelengths may be utilized to distinguish nuisance particles from smoke particles. Furthermore, embodiments of the invention also correct light-detection signals received from the external sampling area based on (1) the specific behavior and properties of the light emitter(s) being utilized and (2) the amount of ambient light. In this manner, smoke detectors in accordance with embodiments of the present invention more correctly identify airborne particles and obstructions without the false positive alarms of conventional systems.

In an aspect, embodiments of the invention feature a method of smoke detection utilizing a smoke detector comprising or consisting essentially of (a) a housing, (b) one or more light emitters, and (c) one or more light detectors. At a first time, a first measurement of light including a first wavelength originating outside the housing is acquired without emitting light of approximately the first wavelength from the one or more light emitters. At a second time later than the first time, a second measurement of light including the first wavelength originating outside the housing is acquired while emitting light of approximately the first wavelength with at least one said light emitter. At a third time later than the second time, a third measurement of light including the first wavelength originating outside the housing is acquired without emitting light of approximately the first wavelength from the one or more light emitters. At a fourth time, a first measurement of light including a second wavelength originating outside the housing is acquired without emitting light of approximately the second wavelength from the one or more light emitters. The second wavelength is longer than the first wavelength. At a fifth time later than the fourth time, a second measurement of light including the second wavelength originating outside the housing is acquired while emitting light of approximately the second wavelength with at least one said light emitter. At a sixth time later than the fifth time, a third measurement of light including the second wavelength originating outside the housing is acquired without emitting light of approximately the second wavelength from the one or more light emitters. (As utilized herein, light "originating outside the housing" includes portions of light originally emitted by one or more of the light emitters and reflected back to one or more of the light detectors from an object or a plurality of particles in the external sampling area, as well as other light (e.g., background light) of the particular wavelength(s) originating from other sources and detected by one or more of the light detectors.) An ambient light level outside of the housing is detected. The second measurement of light including the first wavelength is corrected based on (i) the detected ambient light level and (ii) the first and/or third measurements of light including the first wavelength, thereby producing a corrected first-wavelength measurement. The second measurement of light including the second wavelength is corrected based on (i) the detected ambient light level and (ii) the first and/or third measurements of light including the second wavelength, thereby producing a corrected second-wavelength measurement. The presence of smoke particles outside the housing is determined based on a ratio of the corrected first-wavelength measurement to the corrected second-wavelength measurement.

Embodiments of the invention may include one or more of the following in any of a variety of different combinations. Measurements of light including the first or second wavelength may be broadband measurements of light of a broader range of wavelengths including the first or second wavelengths (e.g., via a broadband detector), or they may be narrowband measurements of light of a narrow band substantially equal to or including the first or second wavelength (e.g., via different narrowband detectors responsive only to particular wavelengths or wavelength ranges). Producing the corrected first-wavelength measurement may include or consist essentially of (i) subtracting from the second measurement of light including the first wavelength an average of the first and third measurements of light including the first wavelength and (ii) adding to the second measurement of light including the first wavelength an offset based on a function of the detected ambient light level. The offset may be based on a linear or polynomial function of the detected ambient light level. Producing the corrected second-wavelength measurement may include or consist essentially of (i) subtracting from the second measurement of light including the second wavelength an average of the first and third measurements of light including the second wavelength and (ii) adding to the second measurement of light including the second wavelength an offset based on a function of the detected ambient light level. The offset may be based on a linear or polynomial function of the detected ambient light level. Determining the presence of smoke particles outside the housing may include or consist essentially of comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold. The first threshold may correspond to a signal level larger than a signal level generated via smoke obscuration outside the housing of approximately 0.5%/foot and/or to a signal level smaller than a signal level generated via smoke obscuration outside the housing of approximately 4%/foot.

The presence of nuisance particles having a larger average diameter than an average diameter of the smoke particles may be determined based on the ratio of the corrected first-wavelength measurement to the corrected second-wavelength measurement. Determining the presence of smoke particles outside the housing may include or consist essentially of comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold, and determining the presence of nuisance particles may include or consist essentially of comparing the ratio of the corrected first-wavelength measurement to the corrected second-wavelength measurement to a second threshold, nuisance particles being determined to be present when the ratio of the corrected first-wavelength measurement to the corrected second-wavelength measurement is smaller than the second threshold. The first threshold may be approximately equal to the second threshold, or the second threshold may be lower than the first threshold.

The presence of an obstruction outside the housing may be determined based on the corrected first-wavelength measurement and/or the corrected second-wavelength measurement. Determining the presence of an obstruction may include or consist essentially of comparing the corrected first-wavelength measurement and/or the corrected second-wavelength measurement to an obstruction threshold, an obstruction being determined to be present when the corrected first-wavelength measurement and/or the corrected second-wavelength measurement is larger than the obstruction threshold. The obstruction threshold may correspond to a signal level not achievable via buildup of smoke during a single measurement cycle of the one or more detectors. (In various embodiments, a single measurement cycle corresponds to the time between measurements acquired by one or more detectors when in a continuous or periodic monitoring mode.) The obstruction threshold may correspond to a signal level larger than a signal level generated via smoke obscuration outside the housing of approximately 40%/foot.

Less than 100 milliseconds, or even less than 1 millisecond, may elapse between the first time and the third time. Less than 100 milliseconds, or even less than 1 millisecond, may elapse between the fourth time and the sixth time. The one or more light emitters may include or consist essentially of a broadband light source emitting light over a range of wavelengths, the first and second wavelengths being within the range of wavelengths. The broadband light source may include or consist essentially of a white light-emitting diode. The one or more light emitters may include or consist essentially of a first light emitter emitting light at the first wavelength and a second light emitter, different from the first light emitter, emitting light at the second wavelength.

The smoke detector may include a proximity sensor. At least one light emitter and/or at least one light detector may be embedded within the proximity sensor. The smoke detector may include an ambient light sensor discrete from the proximity sensor. At least one light detector may be embedded within the ambient light sensor.

Light of the second wavelength may not be emitted at the second time. Light of the first wavelength may not be emitted at the fifth time. The first wavelength may be between approximately 300 nm and approximately 480 nm. The second wavelength may be between approximately 630 nm and approximately 1000 nm. No light may be emitted by any of the light emitters at the first and third times. No light may be emitted by any of the light emitters at the fourth and sixth times.

In another aspect, embodiments of the invention feature a smoke detector including or consisting essentially of a housing, one or more light emitters for emitting, outside the housing, light of a first wavelength and a second wavelength longer than the first wavelength, one or more light detectors for detecting (i) light emitted from the one or more light emitters reflected back to the one or more light detectors, thereby providing measurements of reflected light including the first and second wavelengths, and (ii) an ambient light level outside of the housing, and an evaluation circuit for (i) correcting a measurement of reflected light including the first wavelength based on the detected ambient light level, thereby producing a corrected first-wavelength measurement, (ii) correcting a measurement of reflected light including the second wavelength based on the detected ambient light level, thereby producing a corrected second-wavelength measurement, and (iii) determining the presence of smoke particles outside the housing based on a ratio of the corrected first-wavelength measurement to the corrected second-wavelength measurement.

Embodiments of the invention may include one or more of the following in any of a variety of different combinations. Measurements of light including the first or second wavelength may be broadband measurements of light of a broader range of wavelengths including the first or second wavelengths (e.g., via a broadband detector), or they may be narrowband measurements of light of a narrow band substantially equal to or including the first or second wavelength (e.g., via different narrowband detectors responsive only to particular wavelengths or wavelength ranges). The evaluation circuit may be configured to (via, e.g., controlling components such as the one or more light emitters and the one or more light detectors) (i) at a first time, acquire a first measurement of light including the first wavelength originating outside the housing without emitting light of approximately the first wavelength from the one or more light emitters, (ii) at a second time later than the first time, acquire a second measurement of light including the first wavelength originating outside the housing while emitting light of approximately the first wavelength with at least one said light emitter, (iii) at a third time later than the second time, acquire a third measurement of light including the first wavelength originating outside the housing without emitting light of approximately the first wavelength from the one or more light emitters, (iv) at a fourth time, acquire a first measurement of light including the second wavelength originating outside the housing without emitting light of approximately the second wavelength from the one or more light emitters, (v) at a fifth time later than the fourth time, acquire a second measurement of light including the second wavelength originating outside the housing while emitting light of approximately the second wavelength with at least one said light emitter, (vi) at a sixth time later than the fifth time, acquire a third measurement of light including the second wavelength originating outside the housing without emitting light of approximately the second wavelength from the one or more light emitters, and (vii) detect the ambient light level outside of the housing.

The evaluation circuit may be configured to produce the corrected first-wavelength measurement by (i) subtracting from the second measurement of light including the first wavelength an average of the first and third measurements of light including the first wavelength and (ii) adding to the second measurement of light including the first wavelength a first offset based on a function of the detected ambient light level, and/or produce the corrected second-wavelength measurement by (i) subtracting from the second measurement of light including the second wavelength an average of the first and third measurements of light including the second wavelength and (ii) adding to the second measurement of light including the second wavelength a second offset based on a function of the detected ambient light level. The first offset may be based on a linear or polynomial function of the detected ambient light level. The second offset may be based on a linear or polynomial function of the detected ambient light level. The evaluation circuit may be configured to determine the presence of smoke particles outside the housing by comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold. The first threshold may correspond to a signal level larger than a signal level generated via smoke obscuration outside the housing of approximately 0.5%/foot and/or to a signal level smaller than a signal level generated via smoke obscuration outside the housing of approximately 4%/foot.

The evaluation circuit may be configured to determine, based on the ratio of the corrected first-wavelength measurement to the corrected second-wavelength measurement, the presence of nuisance particles having a larger average diameter than an average diameter of the smoke particles. The evaluation circuit may be configured to (i) determine the presence of smoke particles outside the housing by comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold, and (ii) determine the presence of nuisance particles by comparing the ratio of the corrected first-wavelength measurement to the corrected second-wavelength measurement to a second threshold, nuisance particles being determined to be present when the ratio of the corrected first-wavelength measurement to the corrected second-wavelength measurement is smaller than the second threshold. The first threshold may be approximately equal to the second threshold. The second threshold may be lower than the first threshold.

The evaluation circuit may be configured to determine the presence of an obstruction outside the housing based on the corrected first-wavelength measurement and/or the corrected second-wavelength measurement. The evaluation circuit may be configured to determine the presence of an obstruction by comparing the corrected first-wavelength measurement and/or the corrected second-wavelength measurement to an obstruction threshold, an obstruction being determined to be present when the corrected first-wavelength measurement and/or the corrected second-wavelength measurement is larger than the obstruction threshold. The obstruction threshold may correspond to a signal level not achievable via buildup of smoke during a single measurement cycle of the one or more detectors. The obstruction threshold may correspond to a signal level larger than a signal level generated via smoke obscuration outside the housing of approximately 40%/foot.

At least one light emitter (or even all light emitters) may be at least partially disposed within the housing. The housing may define one or more openings through which light from the light emitter(s) is emitted. The one or more openings may include or consist essentially of a plurality of different openings each associated with at least one light emitter. Each light emitter may emit light through a different opening. The housing may include or consist essentially of one or more solid windows and/or optical elements through which light from the light emitter(s) is emitted. The one or more solid windows may include or consist essentially of a plurality of different solid windows each associated with at least one light emitter. Each light emitter may emit light through a different window or optical element. The one or more light emitters may include or consist essentially of a broadband light source emitting light over a range of wavelengths, the first and second wavelengths being within the range of wavelengths. The broadband light source may include or consist essentially of a white light-emitting diode. The one or more light emitters may include or consist essentially of a first light emitter emitting light at the first wavelength and a second light emitter, different from the first light emitter, emitting light at the second wavelength. The first light emitter may be configured to emit light of the first wavelength only when the second light emitter is not emitting light of the second wavelength, and/or the second light emitter may be configured to emit light of the second wavelength only when the first light emitter is not emitting light of the first wavelength. The smoke detector may include a proximity sensor. At least one light emitter and/or at least one light detector may be embedded within the proximity sensor. The one or more light detectors may include an ambient light sensor discrete from the proximity sensor. The proximity sensor may detect the ambient light level outside the housing (i.e., the proximity sensor may include an ambient light detector therewithin). The first wavelength may be between approximately 300 nm and approximately 480 nm. The second wavelength may be between approximately 630 nm and approximately 1000 nm.

The evaluation circuit may include or consist essentially of a timer for measuring elapsed time, a receiver for (i) receiving signals from at least one light detector at a plurality of different times measured by the timer and (ii) receiving signals based on the detected ambient light level, a controller for controlling at least one light emitter to (i) emit light during at least one of the plurality of times during which light-detection signals are received and (ii) not emit light during at least one other of the plurality of times during which light-detection signals are received, a transformer for producing the corrected first-wavelength measurement and the corrected second-wavelength measurement based on signals received by the receiver, and a signal analyzer for determining the presence of smoke particles outside the housing. The controller may control a first light emitter emitting light of the first wavelength and a second light emitter emitting light of the second wavelength.

The evaluation circuit may be configured to (a) at a first time, acquire a first measurement of light including the first wavelength originating outside the housing while emitting light of approximately the first wavelength with at least one said light emitter, (b) at least one of (i) at a second time earlier than the first time, acquire a second measurement of light including the first wavelength originating outside the housing without emitting light of approximately the first wavelength from the one or more light emitters, or (ii) at a third time later than the first time, acquire a third measurement of light including the first wavelength originating outside the housing without emitting light of approximately the first wavelength from the one or more light emitters, (c) at a fourth time, acquire a first measurement of light including the second wavelength originating outside the housing while emitting light of approximately the second wavelength with at least one said light emitter, (d) at least one of (i) at a fifth time earlier than the fourth time, acquire a second measurement of light including the second wavelength originating outside the housing without emitting light of approximately the second wavelength from the one or more light emitters, or (ii) at a sixth time later than the fourth time, acquire a third measurement of light including the second wavelength originating outside the housing without emitting light of approximately the second wavelength from the one or more light emitters, and (e) detect an ambient light level outside of the housing. The evaluation circuit may be configured to (a) only acquire one of the second or third measurements of light including the first wavelength, and (b) produce the corrected first-wavelength measurement by (i) subtracting from the first measurement of light including the first wavelength the acquired one of the second or third measurements of light including the first wavelength and (ii) adding to the first measurement of light including the first wavelength an offset based on a function of the detected ambient light level. The evaluation circuit may be configured to (a) acquire both of the second and third measurements of light including the first wavelength, and (b) produce the corrected first-wavelength measurement by (i) subtracting from the first measurement of light including the first wavelength an average of the second and third measurements of light including the first wavelength and (ii) adding to the first measurement of light including the first wavelength an offset based on a function of the detected ambient light level. The evaluation circuit may be configured to (a) only acquire one of the second or third measurements of light including the second wavelength, and (b) produce the corrected second-wavelength measurement by (i) subtracting from the first measurement of light including the second wavelength the acquired one of the second or third measurements of light including the second wavelength and (ii) adding to the first measurement of light including the second wavelength an offset based on a function of the detected ambient light level. The evaluation circuit may be configured to (a) acquire both of the second and third measurements of light including the second wavelength, and (b) produce the corrected second-wavelength measurement by (i) subtracting from the first measurement of light including the second wavelength an average of the second and third measurements of light including the second wavelength and (ii) adding to the first measurement of light including the second wavelength an offset based on a function of the detected ambient light level.

The evaluation circuit may be configured to (a) acquire a first unilluminated measurement of light including the first wavelength and the second wavelength originating outside the housing without emitting light of approximately the first wavelength or light of approximately the second wavelength from the one or more light emitters, (b) acquire a measurement of light including the first wavelength originating outside the housing while emitting light of approximately the first wavelength with at least one said light emitter, (c) acquire a measurement of light including the second wavelength originating outside the housing while emitting light of approximately the second wavelength with at least one said light emitter, and (d) detect an ambient light level outside of the housing. The evaluation circuit may be configured to (a) produce the corrected first-wavelength measurement by (i) subtracting from the measurement of light including the first wavelength the first unilluminated measurement of light including the first wavelength and the second wavelength and (ii) adding to the measurement of light including the first wavelength a first offset based on a function of the detected ambient light level, and/or (b) produce the corrected second-wavelength measurement by (i) subtracting from the measurement of light including the second wavelength the first unilluminated measurement of light including the first wavelength and the second wavelength and (ii) adding to the measurement of light including the second wavelength a second offset based on a function of the detected ambient light level. The first offset may be based on a linear or polynomial function of the detected ambient light level. The second offset may be based on a linear or polynomial function of the detected ambient light level.

The evaluation circuit may be configured to acquire the first unilluminated measurement of light including the first wavelength and the second wavelength before the measurement of light including the first wavelength and the measurement of light including the second wavelength are acquired. The evaluation circuit may be configured to acquire at least one of the measurement of light including the first wavelength or the measurement of light including the second wavelength before the first unilluminated measurement of light including the first wavelength and the second wavelength is acquired. The evaluation circuit may be configured to acquire only one of the measurement of light including the first wavelength or the measurement of light including the second wavelength before the first unilluminated measurement of light including the first wavelength and the second wavelength is acquired.

The evaluation circuit may be configured to, after acquiring the first unilluminated measurement of light including the first wavelength and the second wavelength, acquire a second unilluminated measurement of light including the first wavelength and the second wavelength originating outside the housing without emitting light of approximately the first wavelength or light of approximately the second wavelength from the one or more light emitters. The evaluation circuit may be configured to (i) acquire the first unilluminated measurement of light including the first wavelength and the second wavelength before at least one of the measurement of light including the first wavelength or the measurement of light including the second wavelength is acquired, and (ii) acquire the second unilluminated measurement of light including the first wavelength and the second wavelength after at least one of the measurement of light including the first wavelength or the measurement of light including the second wavelength is acquired. The evaluation circuit may be configured to produce the corrected first-wavelength measurement by (i) subtracting from the measurement of light including the first wavelength an average of (a) the first unilluminated measurement of light including the first wavelength and the second wavelength and (b) the second unilluminated measurement of light including the first wavelength and the second wavelength, and (ii) adding to the measurement of light including the first wavelength an offset based on a function of the detected ambient light level. The evaluation circuit may be configured to produce the corrected second-wavelength measurement by (i) subtracting from the measurement of light including the second wavelength an average of (a) the first unilluminated measurement of light including the first wavelength and the second wavelength and (b) the second unilluminated measurement of light including the first wavelength and the second wavelength, and (ii) adding to the measurement of light including the second wavelength an offset based on a function of the detected ambient light level.

In yet another aspect, embodiments of the invention feature a method of smoke detection utilizing a smoke detector including or consisting essentially of (a) a housing, (b) one or more light emitters, and (c) one or more light detectors. At a first time, a first measurement of light including a first wavelength originating outside the housing is acquired while emitting light of approximately the first wavelength with at least one said light emitter. At a second time earlier than the first time, a second measurement of light including the first wavelength originating outside the housing is acquired without emitting light of approximately the first wavelength from the one or more light emitters, and/or, at a third time later than the first time, a third measurement of light including the first wavelength originating outside the housing is acquired without emitting light of approximately the first wavelength from the one or more light emitters. At a fourth time, a first measurement of light including a second wavelength originating outside the housing is acquired while emitting light of approximately the second wavelength with at least one said light emitter. The second wavelength is longer than the first wavelength. At a fifth time earlier than the fourth time, a second measurement of light including the second wavelength originating outside the housing is acquired without emitting light of approximately the second wavelength from the one or more light emitters, and/or at a sixth time later than the fourth time, a third measurement of light including the second wavelength originating outside the housing is acquired without emitting light of approximately the second wavelength from the one or more light emitters. An ambient light level outside of the housing is detected. The first measurement of light including the first wavelength is corrected based on (i) the detected ambient light level and (ii) the second and/or third measurements of light including the first wavelength, thereby producing a corrected first-wavelength measurement. The first measurement of light including the second wavelength is corrected based on (i) the detected ambient light level and (ii) the second and/or third measurements of light including the second wavelength, thereby producing a corrected second-wavelength measurement. The presence of smoke particles outside the housing is determined based on a ratio of the corrected first-wavelength measurement to the corrected second-wavelength measurement.

Embodiments of the invention may include one or more of the following in any of a variety of different combinations. Measurements of light including the first or second wavelength may be broadband measurements of light of a broader range of wavelengths including the first or second wavelengths (e.g., via a broadband detector), or they may be narrowband measurements of light of a narrow band substantially equal to or including the first or second wavelength (e.g., via different narrowband detectors responsive only to particular wavelengths or wavelength ranges). Only one of the second or third measurements of light including the first wavelength may be acquired, and producing the corrected first-wavelength measurement may include or consist essentially of (i) subtracting from the first measurement of light including the first wavelength the acquired one of the second or third measurements of light including the first wavelength and (ii) adding to the first measurement of light including the first wavelength an offset based on a function of the detected ambient light level. The offset may be based on a linear or polynomial function of the detected ambient light level. Both of the second and third measurements of light including the first wavelength may be acquired, and producing the corrected first-wavelength measurement may include or consist essentially of (i) subtracting from the first measurement of light including the first wavelength an average of the second and third measurements of light including the first wavelength and (ii) adding to the first measurement of light including the first wavelength an offset based on a function of the detected ambient light level. The offset may be based on a linear or polynomial function of the detected ambient light level. Only one of the second or third measurements of light including the second wavelength may be acquired, and producing the corrected second-wavelength measurement may include or consist essentially of (i) subtracting from the first measurement of light including the second wavelength the acquired one of the second or third measurements of light including the second wavelength and (ii) adding to the first measurement of light including the second wavelength an offset based on a function of the detected ambient light level. The offset may be based on a linear or polynomial function of the detected ambient light level. Both of the second and third measurements of light including the second wavelength may be acquired, and producing the corrected second-wavelength measurement may include or consist essentially of (i) subtracting from the first measurement of light including the second wavelength an average of the second and third measurements of light including the second wavelength and (ii) adding to the first measurement of light including the second wavelength an offset based on a function of the detected ambient light level. The offset may be based on a linear or polynomial function of the detected ambient light level.

Determining the presence of smoke particles outside the housing may include or consist essentially of comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold. The first threshold may correspond to a signal level larger than a signal level generated via smoke obscuration outside the housing of approximately 0.5%/foot and/or to a signal level smaller than a signal level generated via smoke obscuration outside the housing of approximately 4%/foot.

The presence of nuisance particles having a larger average diameter than an average diameter of the smoke particles may be determined based on the ratio of the corrected first-wavelength measurement to the corrected second-wavelength measurement. Determining the presence of smoke particles outside the housing may include or consist essentially of comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold, and determining the presence of nuisance particles may include or consist essentially of comparing the ratio of the corrected first-wavelength measurement to the corrected second-wavelength measurement to a second threshold, nuisance particles being determined to be present when the ratio of the corrected first-wavelength measurement to the corrected second-wavelength measurement is smaller than the second threshold. The first threshold may be approximately equal to the second threshold. The second threshold may be lower than the first threshold.

The presence of an obstruction outside the housing may be determined based on the corrected first-wavelength measurement and/or the corrected second-wavelength measurement. Determining the presence of an obstruction may include or consist essentially of comparing the corrected first-wavelength measurement and/or the corrected second-wavelength measurement to an obstruction threshold, an obstruction being determined to be present when the corrected first-wavelength measurement and/or the corrected second-wavelength measurement is larger than the obstruction threshold. The obstruction threshold may correspond to a signal level not achievable via buildup of smoke during a single measurement cycle of the one or more detectors. The obstruction threshold may correspond to a signal level larger than a signal level generated via smoke obscuration outside the housing of approximately 40%/foot. The first measurement of light including the first wavelength and the second and/or third measurements of light including the first wavelength may be acquired over a time period less than 100 milliseconds. The first measurement of light including the second wavelength and the second and/or third measurements of light including the second wavelength may be acquired over a time period less than 100 milliseconds. The first measurement of light including the first wavelength and the second and/or third measurements of light including the first wavelength may be acquired over a time period less than 1 millisecond. The first measurement of light including the second wavelength and the second and/or third measurements of light including the second wavelength may be acquired over a time period less than 1 millisecond.

The one or more light emitters may include or consist essentially of a broadband light source emitting light over a range of wavelengths, the first and second wavelengths being within the range of wavelengths. The broadband light source may include or consist essentially of a white light-emitting diode. The one or more light emitters may include or consist essentially of a first light emitter emitting light at the first wavelength and a second light emitter, different from the first light emitter, emitting light at the second wavelength. The smoke detector may include a proximity sensor. At least one light emitter and/or at least one light detector may be portions of and/or embedded within the proximity sensor. The smoke detector may include an ambient light sensor discrete from the proximity sensor. At least one light detector may be part of and/or embedded within the ambient light sensor. Light of the second wavelength may not be emitted at the first time. Light of the first wavelength may not be emitted at the fourth time. The first wavelength may be between approximately 300 nm and approximately 480 nm. The second wavelength may be between approximately 630 nm and approximately 1000 nm. Light may not be emitted by any of the light emitters at the second and third times. Light may not be emitted by any of the light emitters at the fifth and sixth times.

In another aspect, embodiments of the invention feature a method of smoke detection utilizing a smoke detector comprising (a) a housing, (b) one or more light emitters, and (c) one or more light detectors. A first unilluminated measurement of light including a first wavelength and a second wavelength longer than the first wavelength originating outside the housing is acquired without emitting light of approximately the first wavelength or light of approximately the second wavelength from the one or more light emitters. A measurement of light including the first wavelength originating outside the housing is acquired while emitting light of approximately the first wavelength with at least one said light emitter. A measurement of light including the second wavelength originating outside the housing is acquired while emitting light of approximately the second wavelength with at least one said light emitter. An ambient light level outside of the housing is detected. The measurement of light including the first wavelength is corrected based at least in part on (i) the detected ambient light level and (ii) the first unilluminated measurement of light including the first wavelength and the second wavelength, thereby producing a corrected first-wavelength measurement. The measurement of light including the second wavelength is corrected based at least in part on (i) the detected ambient light level and (ii) the first unilluminated measurement of light including the first wavelength and the second wavelength, thereby producing a corrected second-wavelength measurement. The presence of smoke particles outside the housing is determined based on a ratio of the corrected first-wavelength measurement to the corrected second-wavelength measurement.

Embodiments of the invention may include one or more of the following in any of a variety of different combinations. Measurements of light including the first or second wavelength may be broadband measurements of light of a broader range of wavelengths including the first or second wavelengths (e.g., via a broadband detector), or they may be narrowband measurements of light of a narrow band substantially equal to or including the first or second wavelength (e.g., via different narrowband detectors responsive only to particular wavelengths or wavelength ranges). Producing the corrected first-wavelength measurement may include or consist essentially of (i) subtracting from the measurement of light including the first wavelength the first unilluminated measurement of light including the first wavelength and the second wavelength and (ii) adding to the measurement of light including the first wavelength an offset based on a function of the detected ambient light level. The offset may be based on a linear or polynomial function of the detected ambient light level. Producing the corrected second-wavelength measurement may include or consist essentially of (i) subtracting from the measurement of light including the second wavelength the first unilluminated measurement of light including the first wavelength and the second wavelength and (ii) adding to the measurement of light including the second wavelength an offset based on a function of the detected ambient light level. The offset may be based on a linear or polynomial function of the detected ambient light level.

The first unilluminated measurement of light including the first wavelength and the second wavelength may be acquired before the measurement of light including the first wavelength and the measurement of light including the second wavelength are acquired. At least one of the measurement of light including the first wavelength or the measurement of light including the second wavelength may be acquired before the first unilluminated measurement of light including the first wavelength and the second wavelength is acquired. Only one (i.e., either) of the measurement of light including the first wavelength or the measurement of light including the second wavelength may be acquired before the first unilluminated measurement of light including the first wavelength and the second wavelength is acquired.

After acquiring the first unilluminated measurement of light including the first wavelength and the second wavelength, a second unilluminated measurement of light including the first wavelength and the second wavelength originating outside the housing may be acquired without emitting light of approximately the first wavelength or light of approximately the second wavelength from the one or more light emitters. The first unilluminated measurement of light including the first wavelength and the second wavelength may be acquired before at least one of the measurement of light including the first wavelength or the measurement of light including the second wavelength is acquired. The second unilluminated measurement of light including the first wavelength and the second wavelength may be acquired after at least one of the measurement of light including the first wavelength or the measurement of light including the second wavelength is acquired. Producing the corrected first-wavelength measurement may include or consist essentially of (i) subtracting from the measurement of light including the first wavelength an average of (a) the first unilluminated measurement of light including the first wavelength and the second wavelength and (b) the second unilluminated measurement of light including the first wavelength and the second wavelength, and (ii) adding to the measurement of light including the first wavelength an offset based on a function of the detected ambient light level. The offset may be based on a linear or polynomial function of the detected ambient light level. Producing the corrected second-wavelength measurement may include or consist essentially of (i) subtracting from the measurement of light including the second wavelength an average of (a) the first unilluminated measurement of light including the first wavelength and the second wavelength and (b) the second unilluminated measurement of light including the first wavelength and the second wavelength, and (ii) adding to the measurement of light including the second wavelength an offset based on a function of the detected ambient light level. The offset may be based on a linear or polynomial function of the detected ambient light level.

Determining the presence of smoke particles outside the housing may include or consist essentially of comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold. The first threshold may correspond to a signal level larger than a signal level generated via smoke obscuration outside the housing of approximately 0.5%/foot and/or to a signal level smaller than a signal level generated via smoke obscuration outside the housing of approximately 4%/foot.

The presence of nuisance particles having a larger average diameter than an average diameter of the smoke particles may be determined based on the ratio of the corrected first-wavelength measurement to the corrected second-wavelength measurement. Determining the presence of smoke particles outside the housing may include or consist essentially of comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold. Determining the presence of nuisance particles may include or consist essentially of comparing the ratio of the corrected first-wavelength measurement to the corrected second-wavelength measurement to a second threshold, nuisance particles being determined to be present when the ratio of the corrected first-wavelength measurement to the corrected second-wavelength measurement is smaller than the second threshold. The first threshold may be approximately equal to the second threshold. The second threshold may be lower than the first threshold.

The presence of an obstruction outside the housing may be determined based on at least one of the corrected first-wavelength measurement or the corrected second-wavelength measurement. Determining the presence of an obstruction may include or consist essentially of comparing the corrected first-wavelength measurement and/or the corrected second-wavelength measurement to an obstruction threshold, an obstruction being determined to be present when the corrected first-wavelength measurement and/or the corrected second-wavelength measurement is larger than the obstruction threshold. The obstruction threshold may correspond to a signal level not achievable via buildup of smoke during a single measurement cycle of the one or more detectors. The obstruction threshold may correspond to a signal level larger than a signal level generated via smoke obscuration outside the housing of approximately 40%/foot.

The first unilluminated measurement of light including the first wavelength and the second wavelength, the measurement of light including the first wavelength, and the measurement of light including the second wavelength may be acquired over a time period less than 100 milliseconds, or even a time period less than 1 millisecond. The one or more light emitters may include or consist essentially of a broadband light source emitting light over a range of wavelengths, the first and second wavelengths being within the range of wavelengths. The broadband light source may include or consist essentially of a white light-emitting diode. The one or more light emitters may include or consist essentially of a first light emitter emitting light at the first wavelength and a second light emitter, different from the first light emitter, emitting light at the second wavelength. The smoke detector may include a proximity sensor, and at least one light detector may be embedded within the proximity sensor. The smoke detector may include an ambient light sensor discrete from the proximity sensor, and at least one light detector may be embedded within the ambient light sensor. The first wavelength may be between approximately 300 nm and approximately 480 nm (inclusive). The second wavelength may be between approximately 630 nm and approximately 1000 nm (inclusive). Light may not be emitted by any of the one or more light emitters during acquisition of the first unilluminated measurement of light including the first wavelength and the second wavelength.

In another aspect, embodiments of the invention feature a smoke detector including or consisting essentially of a housing, one or more light emitters, one or more light detectors, one or more optical elements, and an evaluation circuit. The one or more light emitters emit, outside the housing, light of a first wavelength and a second wavelength longer than the first wavelength. The one or more light detectors detect (i) light emitted from the one or more light emitters reflected back to the one or more light detectors from a sampling volume outside of the housing, thereby providing measurements of reflected light including the first and second wavelengths, and (ii) an ambient light level outside of the housing. The one or more optical elements are configured (e.g., shaped and/or positioned) to alter a position and/or a size of at least a portion of the sampling volume by altering an emission trajectory of light emitted from at least one of the one or more light emitters. The evaluation circuit (i) corrects a measurement of reflected light including the first wavelength based on the detected ambient light level, thereby producing a corrected first-wavelength measurement, (ii) corrects a measurement of reflected light including the second wavelength based on the detected ambient light level, thereby producing a corrected second-wavelength measurement, and (iii) determines the presence of smoke particles outside the housing based on a ratio of the corrected first-wavelength measurement to the corrected second-wavelength measurement.

Embodiments of the invention may include one or more of the following in any of a variety of different combinations. Measurements of light including the first or second wavelength may be broadband measurements of light of a broader range of wavelengths including the first or second wavelengths (e.g., via a broadband detector), or they may be narrowband measurements of light of a narrow band substantially equal to or including the first or second wavelength (e.g., via different narrowband detectors responsive only to particular wavelengths or wavelength ranges). The evaluation circuit may be configured to (via, e.g., controlling components such as the one or more light emitters and the one or more light detectors) (i) at a first time, acquire a first measurement of light including the first wavelength originating outside the housing without emitting light of approximately the first wavelength from the one or more light emitters, (ii) at a second time later than the first time, acquire a second measurement of light including the first wavelength originating outside the housing while emitting light of approximately the first wavelength with at least one said light emitter, (iii) at a third time later than the second time, acquire a third measurement of light including the first wavelength originating outside the housing without emitting light of approximately the first wavelength from the one or more light emitters, (iv) at a fourth time, acquire a first measurement of light including the second wavelength originating outside the housing without emitting light of approximately the second wavelength from the one or more light emitters, (v) at a fifth time later than the fourth time, acquire a second measurement of light including the second wavelength originating outside the housing while emitting light of approximately the second wavelength with at least one said light emitter, (vi) at a sixth time later than the fifth time, acquire a third measurement of light including the second wavelength originating outside the housing without emitting light of approximately the second wavelength from the one or more light emitters, and (vii) detect the ambient light level outside of the housing.

The evaluation circuit may be configured to produce the corrected first-wavelength measurement by (i) subtracting from the second measurement of light including the first wavelength an average of the first and third measurements of light including the first wavelength and (ii) adding to the second measurement of light including the first wavelength a first offset based on a function of the detected ambient light level, and/or produce the corrected second-wavelength measurement by (i) subtracting from the second measurement of light including the second wavelength an average of the first and third measurements of light including the second wavelength and (ii) adding to the second measurement of light including the second wavelength a second offset based on a function of the detected ambient light level. The first offset may be based on a linear or polynomial function of the detected ambient light level. The second offset may be based on a linear or polynomial function of the detected ambient light level. The evaluation circuit may be configured to determine the presence of smoke particles outside the housing by comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold. The first threshold may correspond to a signal level larger than a signal level generated via smoke obscuration outside the housing of approximately 0.5%/foot and/or to a signal level smaller than a signal level generated via smoke obscuration outside the housing of approximately 4%/foot.

The evaluation circuit may be configured to determine, based on the ratio of the corrected first-wavelength measurement to the corrected second-wavelength measurement, the presence of nuisance particles having a larger average diameter than an average diameter of the smoke particles. The evaluation circuit may be configured to (i) determine the presence of smoke particles outside the housing by comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold, and (ii) determine the presence of nuisance particles by comparing the ratio of the corrected first-wavelength measurement to the corrected second-wavelength measurement to a second threshold, nuisance particles being determined to be present when the ratio of the corrected first-wavelength measurement to the corrected second-wavelength measurement is smaller than the second threshold. The first threshold may be approximately equal to the second threshold. The second threshold may be lower than the first threshold.

The evaluation circuit may be configured to determine the presence of an obstruction outside the housing based on the corrected first-wavelength measurement and/or the corrected second-wavelength measurement. The evaluation circuit may be configured to determine the presence of an obstruction by comparing the corrected first-wavelength measurement and/or the corrected second-wavelength measurement to an obstruction threshold, an obstruction being determined to be present when the corrected first-wavelength measurement and/or the corrected second-wavelength measurement is larger than the obstruction threshold. The obstruction threshold may correspond to a signal level not achievable via buildup of smoke during a single measurement cycle of the one or more detectors. The obstruction threshold may correspond to a signal level larger than a signal level generated via smoke obscuration outside the housing of approximately 40%/foot.

At least one light emitter (or even all light emitters) may be disposed at least partially within the housing. The housing may define one or more openings through which light from the light emitter(s) is emitted. One or more of the light emitters may protrude through the opening(s). The one or more openings may include or consist essentially of a plurality of different openings each associated with at least one light emitter. Each light emitter may emit light through a different opening. The housing may include or consist essentially of one or more solid windows through which light from the light emitter(s) is emitted. The one or more solid windows may include or consist essentially of a plurality of different solid windows each associated with at least one light emitter. Each light emitter may emit light through a different window. The one or more light emitters may include or consist essentially of a broadband light source emitting light over a range of wavelengths, the first and second wavelengths being within the range of wavelengths. The broadband light source may include or consist essentially of a white light-emitting diode. The one or more light emitters may include or consist essentially of a first light emitter emitting light at the first wavelength and a second light emitter, different from the first light emitter, emitting light at the second wavelength. The first light emitter may be configured to emit light of the first wavelength only when the second light emitter is not emitting light of the second wavelength, and/or the second light emitter may be configured to emit light of the second wavelength only when the first light emitter is not emitting light of the first wavelength. The smoke detector may include a proximity sensor. At least one light emitter and/or at least one light detector may be embedded within the proximity sensor. The one or more light detectors may include an ambient light sensor discrete from the proximity sensor. The proximity sensor may detect the ambient light level outside the housing (i.e., the proximity sensor may include an ambient light detector therewithin). The first wavelength may be between approximately 300 nm and approximately 480 nm. The second wavelength may be between approximately 630 nm and approximately 1000 nm.

The evaluation circuit may include or consist essentially of a timer for measuring elapsed time, a receiver for (i) receiving signals from at least one light detector at a plurality of different times measured by the timer and (ii) receiving signals based on the detected ambient light level, a controller for controlling at least one light emitter to (i) emit light during at least one of the plurality of times during which light-detection signals are received and (ii) not emit light during at least one other of the plurality of times during which light-detection signals are received, a transformer for producing the corrected first-wavelength measurement and the corrected second-wavelength measurement based on signals received by the receiver, and a signal analyzer for determining the presence of smoke particles outside the housing. The controller may control a first light emitter emitting light of the first wavelength and a second light emitter emitting light of the second wavelength.

The evaluation circuit may be configured to (a) at a first time, acquire a first measurement of light including the first wavelength originating outside the housing while emitting light of approximately the first wavelength with at least one said light emitter, (b) at least one of (i) at a second time earlier than the first time, acquire a second measurement of light including the first wavelength originating outside the housing without emitting light of approximately the first wavelength from the one or more light emitters, or (ii) at a third time later than the first time, acquire a third measurement of light including the first wavelength originating outside the housing without emitting light of approximately the first wavelength from the one or more light emitters, (c) at a fourth time, acquire a first measurement of light including the second wavelength originating outside the housing while emitting light of approximately the second wavelength with at least one said light emitter, (d) at least one of (i) at a fifth time earlier than the fourth time, acquire a second measurement of light including the second wavelength originating outside the housing without emitting light of approximately the second wavelength from the one or more light emitters, or (ii) at a sixth time later than the fourth time, acquire a third measurement of light including the second wavelength originating outside the housing without emitting light of approximately the second wavelength from the one or more light emitters, and (e) detect an ambient light level outside of the housing. The evaluation circuit may be configured to (a) only acquire one of the second or third measurements of light including the first wavelength, and (b) produce the corrected first-wavelength measurement by (i) subtracting from the first measurement of light including the first wavelength the acquired one of the second or third measurements of light including the first wavelength and (ii) adding to the first measurement of light including the first wavelength an offset based on a function of the detected ambient light level. The evaluation circuit may be configured to (a) acquire both of the second and third measurements of light including the first wavelength, and (b) produce the corrected first-wavelength measurement by (i) subtracting from the first measurement of light including the first wavelength an average of the second and third measurements of light including the first wavelength and (ii) adding to the first measurement of light including the first wavelength an offset based on a function of the detected ambient light level. The evaluation circuit may be configured to (a) only acquire one of the second or third measurements of light including the second wavelength, and (b) produce the corrected second-wavelength measurement by (i) subtracting from the first measurement of light including the second wavelength the acquired one of the second or third measurements of light including the second wavelength and (ii) adding to the first measurement of light including the second wavelength an offset based on a function of the detected ambient light level. The evaluation circuit may be configured to (a) acquire both of the second and third measurements of light including the second wavelength, and (b) produce the corrected second-wavelength measurement by (i) subtracting from the first measurement of light including the second wavelength an average of the second and third measurements of light including the second wavelength and (ii) adding to the first measurement of light including the second wavelength an offset based on a function of the detected ambient light level.

The evaluation circuit may be configured to (a) acquire a first unilluminated measurement of light including the first wavelength and the second wavelength originating outside the housing without emitting light of approximately the first wavelength or light of approximately the second wavelength from the one or more light emitters, (b) acquire a measurement of light including the first wavelength originating outside the housing while emitting light of approximately the first wavelength with at least one said light emitter, (c) acquire a measurement of light including the second wavelength originating outside the housing while emitting light of approximately the second wavelength with at least one said light emitter, and (d) detect an ambient light level outside of the housing. The evaluation circuit may be configured to (a) produce the corrected first-wavelength measurement by (i) subtracting from the measurement of light including the first wavelength the first unilluminated measurement of light including the first wavelength and the second wavelength and (ii) adding to the measurement of light including the first wavelength a first offset based on a function of the detected ambient light level, and/or (b) produce the corrected second-wavelength measurement by (i) subtracting from the measurement of light including the second wavelength the first unilluminated measurement of light including the first wavelength and the second wavelength and (ii) adding to the measurement of light including the second wavelength a second offset based on a function of the detected ambient light level. The first offset may be based on a linear or polynomial function of the detected ambient light level. The second offset may be based on a linear or polynomial function of the detected ambient light level.

The evaluation circuit may be configured to acquire the first unilluminated measurement of light including the first wavelength and the second wavelength before the measurement of light including the first wavelength and the measurement of light including the second wavelength are acquired. The evaluation circuit may be configured to acquire at least one of the measurement of light including the first wavelength or the measurement of light including the second wavelength before the first unilluminated measurement of light including the first wavelength and the second wavelength is acquired. The evaluation circuit may be configured to acquire only one of the measurement of light including the first wavelength or the measurement of light including the second wavelength before the first unilluminated measurement of light including the first wavelength and the second wavelength is acquired.

The evaluation circuit may be configured to, after acquiring the first unilluminated measurement of light including the first wavelength and the second wavelength, acquire a second unilluminated measurement of light including the first wavelength and the second wavelength originating outside the housing without emitting light of approximately the first wavelength or light of approximately the second wavelength from the one or more light emitters. The evaluation circuit may be configured to (i) acquire the first unilluminated measurement of light including the first wavelength and the second wavelength before at least one of the measurement of light including the first wavelength or the measurement of light including the second wavelength is acquired, and (ii) acquire the second unilluminated measurement of light including the first wavelength and the second wavelength after at least one of the measurement of light including the first wavelength or the measurement of light including the second wavelength is acquired. The evaluation circuit may be configured to produce the corrected first-wavelength measurement by (i) subtracting from the measurement of light including the first wavelength an average of (a) the first unilluminated measurement of light including the first wavelength and the second wavelength and (b) the second unilluminated measurement of light including the first wavelength and the second wavelength, and (ii) adding to the measurement of light including the first wavelength an offset based on a function of the detected ambient light level. The evaluation circuit may be configured to produce the corrected second-wavelength measurement by (i) subtracting from the measurement of light including the second wavelength an average of (a) the first unilluminated measurement of light including the first wavelength and the second wavelength and (b) the second unilluminated measurement of light including the first wavelength and the second wavelength, and (ii) adding to the measurement of light including the second wavelength an offset based on a function of the detected ambient light level.

The one or more optical elements may be configured to position at least a portion of the sampling volume directly over at least one of the one or more light detectors (and/or the proximity sensor, if the smoke detector includes a proximity sensor). The one or more optical elements may include or consist essentially of a lens, a prism, a grating, and/or a mirror.

In another aspect, embodiments of the invention feature a method of smoke detection utilizing a smoke detector comprising (a) a housing, (b) one or more light emitters, and (c) one or more light detectors. A measurement of light including a first wavelength originating from a first sampling volume outside the housing is acquired while (i) emitting light of approximately the first wavelength with at least one said light emitter and (ii) altering a position of at least a portion of the first sampling volume by altering an emission trajectory of the emitted light of approximately the first wavelength. A measurement of light including a second wavelength originating from a second sampling volume outside the housing is acquired while (i) emitting light of approximately the second wavelength with at least one said light emitter and (ii) altering a position of at least a portion of the second sampling volume by altering an emission trajectory of the emitted light of approximately the second wavelength. The second wavelength is longer than the first wavelength. The first and sampling volumes may be substantially the same or may be different (i.e., may or may not be partially or fully overlapping in space). An ambient light level outside of the housing is detected. The measurement of light including the first wavelength is corrected based at least in part on the detected ambient light level, thereby producing a corrected first-wavelength measurement. The measurement of light including the second wavelength is corrected based at least in part on the detected ambient light level, thereby producing a corrected second-wavelength measurement. The presence of smoke particles outside the housing is determined based on a ratio of the corrected first-wavelength measurement to the corrected second-wavelength measurement. In some embodiments of the invention, the position of at least a portion of only one of the first or second sampling volumes is altered via, e.g., altering the emission trajectory of the emitted light of the first or second wavelength, while the other remains substantially unaltered.

Embodiments of the invention may include one or more of the following in any of a variety of different combinations. Producing the corrected first-wavelength measurement may include or consist essentially of adding to the measurement of light including the first wavelength a first offset based on a function of the detected ambient light level. Producing the corrected second-wavelength measurement may include or consist essentially of adding to the measurement of light including the first wavelength a second offset based on a function of the detected ambient light level. The first offset may be based on a linear or polynomial function of the detected ambient light level. The second offset may be based on a linear or polynomial function of the detected ambient light level. Determining the presence of smoke particles outside the housing may include or consist essentially of comparing the ratio of the corrected first-wavelength measurement to the corrected second-wavelength measurement to a first threshold, and smoke particles may be determined to be present when the ratio of the corrected first-wavelength measurement to the corrected second-wavelength measurement is larger than the first threshold. The first threshold may correspond to (i) a signal level larger than a signal level generated via smoke obscuration outside the housing of approximately 0.5%/foot and/or (ii) a signal level smaller than a signal level generated via smoke obscuration outside the housing of approximately 4%/foot.

The presence of nuisance particles having a larger average diameter than an average diameter of the smoke particles may be determined based on the ratio of the corrected first-wavelength measurement to the corrected second-wavelength measurement. Determining the presence of smoke particles outside the housing may include or consist essentially of comparing the ratio of the corrected first-wavelength measurement to the corrected second-wavelength measurement to a first threshold, and smoke particles may be determined to be present when the ratio of the corrected first-wavelength measurement to the corrected second-wavelength measurement is larger than the first threshold. Determining the presence of nuisance particles may include or consist essentially of comparing the ratio of the corrected first-wavelength measurement to the corrected second-wavelength measurement to a second threshold, and nuisance particles may be determined to be present when the ratio of the corrected first-wavelength measurement to the corrected second-wavelength measurement is smaller than the second threshold. The first threshold may be approximately equal to or lower than the second threshold.

The presence of an obstruction outside the housing may be determined at least in part by comparing at least one of the corrected first-wavelength measurement or the corrected second-wavelength measurement to an obstruction threshold, and an obstruction may be determined to be present when at least one of the corrected first-wavelength measurement or the corrected second-wavelength measurement is larger than the obstruction threshold. The obstruction threshold may correspond to (i) a signal level not achievable via buildup of smoke during a single measurement cycle of the one or more detectors and/or (ii) a signal level larger than a signal level generated via smoke obscuration outside the housing of approximately 40%/foot.

The one or more light emitters may include or consist essentially of a broadband light source emitting light over a range of wavelengths, the first and second wavelengths being within the range of wavelengths. The broadband light source may include or consist essentially of one or more white light-emitting diodes. The one or more light emitters may include or consist essentially of a first light emitter emitting light at the first wavelength and a second light emitter, different from the first light emitter, emitting light at the second wavelength. The smoke detector may include a proximity sensor, and at least one said light detector may be embedded within the proximity sensor. The smoke detector may include an ambient light sensor discrete from the proximity sensor, and at least one said light detector may be embedded within the ambient light sensor. The first wavelength may be between approximately 300 nm and approximately 480 nm. The second wavelength may be between approximately 630 nm and approximately 1000 nm.

A first unilluminated measurement of light including the first wavelength and the second wavelength originating outside the housing may be acquired without emitting light of approximately the first wavelength or light of approximately the second wavelength from the one or more light emitters. Producing the corrected first-wavelength measurement may include or consist essentially of subtracting from the measurement of light including the first wavelength the first unilluminated measurement of light including the first wavelength and the second wavelength. Producing the corrected second-wavelength measurement may include or consist essentially of subtracting from the measurement of light including the second wavelength the first unilluminated measurement of light including the first wavelength and the second wavelength. The first unilluminated measurement of light including the first wavelength and the second wavelength may be acquired before the measurement of light including the first wavelength and the measurement of light including the second wavelength are acquired. The measurement of light including the first wavelength and/or the measurement of light including the second wavelength may be acquired before the first unilluminated measurement of light including the first wavelength and the second wavelength is acquired. The first unilluminated measurement of light including the first wavelength and the second wavelength may be acquired after the measurement of light including the first wavelength and the measurement of light including the second wavelength are acquired.

The emission trajectory of the emitted light of approximately the first wavelength and/or the emission trajectory of the emitted light of approximately the second wavelength may be altered by one or more optical elements. The one or more optical elements may include or consist essentially of a lens, a prism, a grating, or a mirror. At least a portion of the first sampling volume may be disposed directly over at least one of the one or more light detectors. At least a portion of the second sampling volume may be disposed directly over at least one of the one or more light detectors.

In another aspect, embodiments of the invention feature a smoke detector including or consisting essentially of a housing, one or more light emitters, one or more light detectors, and an evaluation circuit. The one or more light emitters emit, outside the housing, light of a first wavelength and a second wavelength longer than the first wavelength. A portion of at least one of the light emitters is disposed substantially flush with a surface of the housing or protrudes out of the housing. The one or more light detectors detect (i) light emitted from the one or more light emitters reflected back to the one or more light detectors from a sampling volume outside of the housing, thereby providing measurements of reflected light including the first and second wavelengths, and (ii) an ambient light level outside of the housing. The evaluation circuit (i) corrects a measurement of reflected light including the first wavelength based on the detected ambient light level, thereby producing a corrected first-wavelength measurement, (ii) corrects a measurement of reflected light including the second wavelength based on the detected ambient light level, thereby producing a corrected second-wavelength measurement, and (iii) determines the presence of smoke particles outside the housing based on a ratio of the corrected first-wavelength measurement to the corrected second-wavelength measurement.

Embodiments of the invention may include one or more of the following in any of a variety of different combinations. Measurements of light including the first or second wavelength may be broadband measurements of light of a broader range of wavelengths including the first or second wavelengths (e.g., via a broadband detector), or they may be narrowband measurements of light of a narrow band substantially equal to or including the first or second wavelength (e.g., via different narrowband detectors responsive only to particular wavelengths or wavelength ranges). The evaluation circuit may be configured to (via, e.g., controlling components such as the one or more light emitters and the one or more light detectors) (i) at a first time, acquire a first measurement of light including the first wavelength originating outside the housing without emitting light of approximately the first wavelength from the one or more light emitters, (ii) at a second time later than the first time, acquire a second measurement of light including the first wavelength originating outside the housing while emitting light of approximately the first wavelength with at least one said light emitter, (iii) at a third time later than the second time, acquire a third measurement of light including the first wavelength originating outside the housing without emitting light of approximately the first wavelength from the one or more light emitters, (iv) at a fourth time, acquire a first measurement of light including the second wavelength originating outside the housing without emitting light of approximately the second wavelength from the one or more light emitters, (v) at a fifth time later than the fourth time, acquire a second measurement of light including the second wavelength originating outside the housing while emitting light of approximately the second wavelength with at least one said light emitter, (vi) at a sixth time later than the fifth time, acquire a third measurement of light including the second wavelength originating outside the housing without emitting light of approximately the second wavelength from the one or more light emitters, and (vii) detect the ambient light level outside of the housing.

The evaluation circuit may be configured to produce the corrected first-wavelength measurement by (i) subtracting from the second measurement of light including the first wavelength an average of the first and third measurements of light including the first wavelength and (ii) adding to the second measurement of light including the first wavelength a first offset based on a function of the detected ambient light level, and/or produce the corrected second-wavelength measurement by (i) subtracting from the second measurement of light including the second wavelength an average of the first and third measurements of light including the second wavelength and (ii) adding to the second measurement of light including the second wavelength a second offset based on a function of the detected ambient light level. The first offset may be based on a linear or polynomial function of the detected ambient light level. The second offset may be based on a linear or polynomial function of the detected ambient light level. The evaluation circuit may be configured to determine the presence of smoke particles outside the housing by comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold. The first threshold may correspond to a signal level larger than a signal level generated via smoke obscuration outside the housing of approximately 0.5%/foot and/or to a signal level smaller than a signal level generated via smoke obscuration outside the housing of approximately 4%/foot.

The evaluation circuit may be configured to determine, based on the ratio of the corrected first-wavelength measurement to the corrected second-wavelength measurement, the presence of nuisance particles having a larger average diameter than an average diameter of the smoke particles. The evaluation circuit may be configured to (i) determine the presence of smoke particles outside the housing by comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold, and (ii) determine the presence of nuisance particles by comparing the ratio of the corrected first-wavelength measurement to the corrected second-wavelength measurement to a second threshold, nuisance particles being determined to be present when the ratio of the corrected first-wavelength measurement to the corrected second-wavelength measurement is smaller than the second threshold. The first threshold may be approximately equal to the second threshold. The second threshold may be lower than the first threshold.

The evaluation circuit may be configured to determine the presence of an obstruction outside the housing based on the corrected first-wavelength measurement and/or the corrected second-wavelength measurement. The evaluation circuit may be configured to determine the presence of an obstruction by comparing the corrected first-wavelength measurement and/or the corrected second-wavelength measurement to an obstruction threshold, an obstruction being determined to be present when the corrected first-wavelength measurement and/or the corrected second-wavelength measurement is larger than the obstruction threshold. The obstruction threshold may correspond to a signal level not achievable via buildup of smoke during a single measurement cycle of the one or more detectors. The obstruction threshold may correspond to a signal level larger than a signal level generated via smoke obscuration outside the housing of approximately 40%/foot.

The housing may define one or more openings through which the portion of at least one said light emitter protrudes or within which the portion of at least one said light emitter is substantially flush with a surface of the housing. The one or more openings may include or consist essentially of a plurality of different openings each associated with at least one light emitter. Each light emitter may partially protrude through a different opening. The one or more light emitters may include or consist essentially of a broadband light source emitting light over a range of wavelengths, the first and second wavelengths being within the range of wavelengths. The broadband light source may include or consist essentially of a white light-emitting diode. The one or more light emitters may include or consist essentially of a first light emitter emitting light at the first wavelength and a second light emitter, different from the first light emitter, emitting light at the second wavelength. The first light emitter may be configured to emit light of the first wavelength only when the second light emitter is not emitting light of the second wavelength, and/or the second light emitter may be configured to emit light of the second wavelength only when the first light emitter is not emitting light of the first wavelength. The smoke detector may include a proximity sensor. At least one light emitter and/or at least one light detector may be embedded within the proximity sensor. The one or more light detectors may include an ambient light sensor discrete from the proximity sensor. The proximity sensor may detect the ambient light level outside the housing (i.e., the proximity sensor may include an ambient light detector therewithin). The first wavelength may be between approximately 300 nm and approximately 480 nm. The second wavelength may be between approximately 630 nm and approximately 1000 nm.

The evaluation circuit may include or consist essentially of a timer for measuring elapsed time, a receiver for (i) receiving signals from at least one light detector at a plurality of different times measured by the timer and (ii) receiving signals based on the detected ambient light level, a controller for controlling at least one light emitter to (i) emit light during at least one of the plurality of times during which light-detection signals are received and (ii) not emit light during at least one other of the plurality of times during which light-detection signals are received, a transformer for producing the corrected first-wavelength measurement and the corrected second-wavelength measurement based on signals received by the receiver, and a signal analyzer for determining the presence of smoke particles outside the housing. The controller may control a first light emitter emitting light of the first wavelength and a second light emitter emitting light of the second wavelength.

The evaluation circuit may be configured to (a) at a first time, acquire a first measurement of light including the first wavelength originating outside the housing while emitting light of approximately the first wavelength with at least one said light emitter, (b) at least one of (i) at a second time earlier than the first time, acquire a second measurement of light including the first wavelength originating outside the housing without emitting light of approximately the first wavelength from the one or more light emitters, or (ii) at a third time later than the first time, acquire a third measurement of light including the first wavelength originating outside the housing without emitting light of approximately the first wavelength from the one or more light emitters, (c) at a fourth time, acquire a first measurement of light including the second wavelength originating outside the housing while emitting light of approximately the second wavelength with at least one said light emitter, (d) at least one of (i) at a fifth time earlier than the fourth time, acquire a second measurement of light including the second wavelength originating outside the housing without emitting light of approximately the second wavelength from the one or more light emitters, or (ii) at a sixth time later than the fourth time, acquire a third measurement of light including the second wavelength originating outside the housing without emitting light of approximately the second wavelength from the one or more light emitters, and (e) detect an ambient light level outside of the housing. The evaluation circuit may be configured to (a) only acquire one of the second or third measurements of light including the first wavelength, and (b) produce the corrected first-wavelength measurement by (i) subtracting from the first measurement of light including the first wavelength the acquired one of the second or third measurements of light including the first wavelength and (ii) adding to the first measurement of light including the first wavelength an offset based on a function of the detected ambient light level. The evaluation circuit may be configured to (a) acquire both of the second and third measurements of light including the first wavelength, and (b) produce the corrected first-wavelength measurement by (i) subtracting from the first measurement of light including the first wavelength an average of the second and third measurements of light including the first wavelength and (ii) adding to the first measurement of light including the first wavelength an offset based on a function of the detected ambient light level. The evaluation circuit may be configured to (a) only acquire one of the second or third measurements of light including the second wavelength, and (b) produce the corrected second-wavelength measurement by (i) subtracting from the first measurement of light including the second wavelength the acquired one of the second or third measurements of light including the second wavelength and (ii) adding to the first measurement of light including the second wavelength an offset based on a function of the detected ambient light level. The evaluation circuit may be configured to (a) acquire both of the second and third measurements of light including the second wavelength, and (b) produce the corrected second-wavelength measurement by (i) subtracting from the first measurement of light including the second wavelength an average of the second and third measurements of light including the second wavelength and (ii) adding to the first measurement of light including the second wavelength an offset based on a function of the detected ambient light level.

The evaluation circuit may be configured to (a) acquire a first unilluminated measurement of light including the first wavelength and the second wavelength originating outside the housing without emitting light of approximately the first wavelength or light of approximately the second wavelength from the one or more light emitters, (b) acquire a measurement of light including the first wavelength originating outside the housing while emitting light of approximately the first wavelength with at least one said light emitter, (c) acquire a measurement of light including the second wavelength originating outside the housing while emitting light of approximately the second wavelength with at least one said light emitter, and (d) detect an ambient light level outside of the housing. The evaluation circuit may be configured to (a) produce the corrected first-wavelength measurement by (i) subtracting from the measurement of light including the first wavelength the first unilluminated measurement of light including the first wavelength and the second wavelength and (ii) adding to the measurement of light including the first wavelength a first offset based on a function of the detected ambient light level, and/or (b) produce the corrected second-wavelength measurement by (i) subtracting from the measurement of light including the second wavelength the first unilluminated measurement of light including the first wavelength and the second wavelength and (ii) adding to the measurement of light including the second wavelength a second offset based on a function of the detected ambient light level. The first offset may be based on a linear or polynomial function of the detected ambient light level. The second offset may be based on a linear or polynomial function of the detected ambient light level.

The evaluation circuit may be configured to acquire the first unilluminated measurement of light including the first wavelength and the second wavelength before the measurement of light including the first wavelength and the measurement of light including the second wavelength are acquired. The evaluation circuit may be configured to acquire at least one of the measurement of light including the first wavelength or the measurement of light including the second wavelength before the first unilluminated measurement of light including the first wavelength and the second wavelength is acquired. The evaluation circuit may be configured to acquire only one of the measurement of light including the first wavelength or the measurement of light including the second wavelength before the first unilluminated measurement of light including the first wavelength and the second wavelength is acquired.

The evaluation circuit may be configured to, after acquiring the first unilluminated measurement of light including the first wavelength and the second wavelength, acquire a second unilluminated measurement of light including the first wavelength and the second wavelength originating outside the housing without emitting light of approximately the first wavelength or light of approximately the second wavelength from the one or more light emitters. The evaluation circuit may be configured to (i) acquire the first unilluminated measurement of light including the first wavelength and the second wavelength before at least one of the measurement of light including the first wavelength or the measurement of light including the second wavelength is acquired, and (ii) acquire the second unilluminated measurement of light including the first wavelength and the second wavelength after at least one of the measurement of light including the first wavelength or the measurement of light including the second wavelength is acquired. The evaluation circuit may be configured to produce the corrected first-wavelength measurement by (i) subtracting from the measurement of light including the first wavelength an average of (a) the first unilluminated measurement of light including the first wavelength and the second wavelength and (b) the second unilluminated measurement of light including the first wavelength and the second wavelength, and (ii) adding to the measurement of light including the first wavelength an offset based on a function of the detected ambient light level. The evaluation circuit may be configured to produce the corrected second-wavelength measurement by (i) subtracting from the measurement of light including the second wavelength an average of (a) the first unilluminated measurement of light including the first wavelength and the second wavelength and (b) the second unilluminated measurement of light including the first wavelength and the second wavelength, and (ii) adding to the measurement of light including the second wavelength an offset based on a function of the detected ambient light level.

The smoke detector may include one or more optical elements configured to alter a position (and/or size) of at least a portion of the sampling volume by, e.g., altering an emission trajectory of light emitted from at least one of the one or more light emitters. The one or more optical elements may be configured to position at least a portion of the sampling volume directly over at least one of the one or more light detectors (and/or the proximity sensor, if the smoke detector includes a proximity sensor). The one or more optical elements may include or consist essentially of a lens, a prism, a grating, and/or a mirror. A portion of one or more (or even all) of the light emitters may protrude out of the housing.

In another aspect, embodiments of the invention feature a method of smoke detection utilizing a smoke detector comprising (a) a housing, (b) one or more light emitters, and (c) one or more light detectors. A measurement of light including a first wavelength originating from a first sampling volume outside the housing is acquired while emitting light of approximately the first wavelength with at least one said light emitter. A measurement of light including a second wavelength originating from a second sampling volume outside the housing is acquired while emitting light of approximately the second wavelength with at least one said light emitter. The second wavelength is longer than the first wavelength. The first and sampling volumes may be substantially the same or may be different (i.e., may or may not be partially or fully overlapping in space). An ambient light level outside of the housing is detected. The measurement of light including the first wavelength is corrected based at least in part on the detected ambient light level, thereby producing a corrected first-wavelength measurement. The measurement of light including the second wavelength is corrected based at least in part on the detected ambient light level, thereby producing a corrected second-wavelength measurement. The presence of smoke particles outside the housing is determined based on a ratio of the corrected first-wavelength measurement to the corrected second-wavelength measurement. A portion of at least one light emitter is disposed substantially flush with a surface of the housing or protrudes out of the housing.

Embodiments of the invention may include one or more of the following in any of a variety of different combinations. Producing the corrected first-wavelength measurement may include or consist essentially of adding to the measurement of light including the first wavelength a first offset based on a function of the detected ambient light level. Producing the corrected second-wavelength measurement may include or consist essentially of adding to the measurement of light including the first wavelength a second offset based on a function of the detected ambient light level. The first offset may be based on a linear or polynomial function of the detected ambient light level. The second offset may be based on a linear or polynomial function of the detected ambient light level. Determining the presence of smoke particles outside the housing may include or consist essentially of comparing the ratio of the corrected first-wavelength measurement to the corrected second-wavelength measurement to a first threshold, and smoke particles may be determined to be present when the ratio of the corrected first-wavelength measurement to the corrected second-wavelength measurement is larger than the first threshold. The first threshold may correspond to (i) a signal level larger than a signal level generated via smoke obscuration outside the housing of approximately 0.5%/foot and/or (ii) a signal level smaller than a signal level generated via smoke obscuration outside the housing of approximately 4%/foot.

The presence of nuisance particles having a larger average diameter than an average diameter of the smoke particles may be determined based on the ratio of the corrected first-wavelength measurement to the corrected second-wavelength measurement. Determining the presence of smoke particles outside the housing may include or consist essentially of comparing the ratio of the corrected first-wavelength measurement to the corrected second-wavelength measurement to a first threshold, and smoke particles may be determined to be present when the ratio of the corrected first-wavelength measurement to the corrected second-wavelength measurement is larger than the first threshold. Determining the presence of nuisance particles may include or consist essentially of comparing the ratio of the corrected first-wavelength measurement to the corrected second-wavelength measurement to a second threshold, and nuisance particles may be determined to be present when the ratio of the corrected first-wavelength measurement to the corrected second-wavelength measurement is smaller than the second threshold. The first threshold may be approximately equal to or lower than the second threshold.

The presence of an obstruction outside the housing may be determined at least in part by comparing at least one of the corrected first-wavelength measurement or the corrected second-wavelength measurement to an obstruction threshold, and an obstruction may be determined to be present when at least one of the corrected first-wavelength measurement or the corrected second-wavelength measurement is larger than the obstruction threshold. The obstruction threshold may correspond to (i) a signal level not achievable via buildup of smoke during a single measurement cycle of the one or more detectors and/or (ii) a signal level larger than a signal level generated via smoke obscuration outside the housing of approximately 40%/foot.

The one or more light emitters may include or consist essentially of a broadband light source emitting light over a range of wavelengths, the first and second wavelengths being within the range of wavelengths. The broadband light source may include or consist essentially of one or more white light-emitting diodes. The one or more light emitters may include or consist essentially of a first light emitter emitting light at the first wavelength and a second light emitter, different from the first light emitter, emitting light at the second wavelength. The smoke detector may include a proximity sensor, and at least one said light detector may be embedded within the proximity sensor. The smoke detector may include an ambient light sensor discrete from the proximity sensor, and at least one said light detector may be embedded within the ambient light sensor. The first wavelength may be between approximately 300 nm and approximately 480 nm. The second wavelength may be between approximately 630 nm and approximately 1000 nm.

A first unilluminated measurement of light including the first wavelength and the second wavelength originating outside the housing may be acquired without emitting light of approximately the first wavelength or light of approximately the second wavelength from the one or more light emitters. Producing the corrected first-wavelength measurement may include or consist essentially of subtracting from the measurement of light including the first wavelength the first unilluminated measurement of light including the first wavelength and the second wavelength. Producing the corrected second-wavelength measurement may include or consist essentially of subtracting from the measurement of light including the second wavelength the first unilluminated measurement of light including the first wavelength and the second wavelength. The first unilluminated measurement of light including the first wavelength and the second wavelength may be acquired before the measurement of light including the first wavelength and the measurement of light including the second wavelength are acquired. The measurement of light including the first wavelength and/or the measurement of light including the second wavelength may be acquired before the first unilluminated measurement of light including the first wavelength and the second wavelength is acquired. The first unilluminated measurement of light including the first wavelength and the second wavelength may be acquired after the measurement of light including the first wavelength and the measurement of light including the second wavelength are acquired.

While acquiring the measurement of light including the first wavelength originating from the first sampling volume outside the housing, the position and/or size of at least a portion of the first sampling volume may be altered by altering an emission trajectory of the emitted light of approximately the first wavelength. While acquiring the measurement of light including the second wavelength originating from the second sampling volume outside the housing, the position and/or size of at least a portion of the second sampling volume may be altered by altering an emission trajectory of the emitted light of approximately the second wavelength. The emission trajectory of the emitted light of approximately the first wavelength and/or the emission trajectory of the emitted light of approximately the second wavelength may be altered by one or more optical elements. The one or more optical elements may include or consist essentially of a lens, a prism, a grating, or a mirror. At least a portion of the first sampling volume may be disposed directly over at least one of the one or more light detectors. At least a portion of the second sampling volume may be disposed directly over at least one of the one or more light detectors. In some embodiments of the invention, the position of at least a portion of only one of the first or second sampling volumes is altered via, e.g., altering the emission trajectory of the emitted light of the first or second wavelength, while the other remains substantially unaltered.

Embodiments of any of the above aspects of the invention may include one or more of the following in any of a variety of combinations. One or more light emitters may be configured to (i) emit a first light portion outside of the housing and (ii) emit a second light portion within the housing substantially without emission therefrom. One or more light detectors may be configured to receive light from the first light portion reflected back into the housing and light from the second light portion within the housing. The evaluation circuit may determine the presence of smoke particles outside the housing based in part on (i) the light received by the one or more light detectors from the first light portion and (ii) the light received by the one or more light detectors from the second light portion. The presence of smoke particles outside the housing may be determined based in part on (i) a luminance and/or a rate of change of luminance of light received from the first light portion, and (ii) a luminance of light received from the second light portion. Light from the second light portion may be reflected by a portion of the housing proximate an opening in the housing. Light from the second light portion may be reflected by a window and/or an optical element in the housing. One or more light emitters and/or one or more light detectors may be portions of a single electronic component, e.g., a proximity sensor. One or more light emitters and/or one or more light detectors may not be portions of a single electronic component (and may thus be separate electronic components that are independently operable). A gas sensor may be disposed at least partially within or on the housing. The presence of smoke particles outside the housing may be determined based in part on (i) a gas concentration sensed by the gas sensor and/or (ii) a temporal evolution of the gas concentration sensed by the gas sensor. The gas sensor may be configured to sense carbon monoxide and/or carbon dioxide. A manual test button may be disposed on the housing and electrically connected to the evaluation circuit. After actuation of the manual test button, the evaluation circuit may perform a test sequence. The test sequence may be based at least in part on the luminance of the received first light portion and the luminance of the received second light portion, and/or the corrected first-wavelength measurement and the corrected second-wavelength measurement. The one or more light detectors may include or consist essentially of a plurality of light detectors each sensitive to light over only a portion of a range of wavelengths emitted by the one or more light emitters. The ambient-light sensor may sense visible and/or infrared light. Light reflected from the first light portion and light from the second light portion may be detected by the same light detector. A maintenance alarm may be activated if a luminance of the detected light from the second light portion falls below a maintenance threshold. A gas concentration outside the housing, e.g., a concentration of carbon monoxide and/or carbon dioxide, may be sensed. The presence of smoke particles outside the housing may be determined based in part on the sensed gas concentration.

These and other objects, along with advantages and features of the invention, will become more apparent through reference to the following description, the accompanying drawings, and the claims. Furthermore, it is to be understood that the features of the various embodiments described herein are not mutually exclusive and can exist in various combinations and permutations. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The term "light" broadly connotes any wavelength or wavelength band in the electromagnetic spectrum, including, without limitation, visible light, ultraviolet radiation, and infrared radiation. Similarly, photometric terms such as "luminance," "luminous flux," and "luminous intensity" extend to and include their radiometric equivalents, such as "radiance," "radiant flux," and "radiant intensity." As used herein, a "portion of light" means an intensity or directional fraction of light that may or may not be discrete from other portions of the same light. As used herein, the term "substantially" means±10%, and in some embodiments, ±5%. The term "consists essentially of" means excluding other materials that contribute to function, unless otherwise defined herein. Nonetheless, such other materials may be present, collectively or individually, in trace amounts.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Discrimination between smoke particles and nuisance particles may be achieved by generating multiple signals each using distinct wavelengths of light. Airborne particles other than smoke, such as dust, powders, cooking aerosols, or water vapor, scatter the various wavelengths of light throughout the near ultraviolet, visible, and near infrared (e.g., wavelengths of approximately 300-1000 nm) generally equally because these particles have a diameter on the order of several microns. However, smoke particles, which typically have a diameter of less than one micron, typically scatter the shorter wavelengths of light much more strongly than the longer wavelengths. By using multiple light emitters, at least one with a shorter emission wavelength, such as blue, violet, or ultraviolet (e.g., wavelengths of approximately 300-480 nm), and at least one with a longer emission wavelength, such as red or infrared (e.g., wavelengths of approximately 630-1000 nm), the relative signals may be compared to determine whether the airborne particles within the external sampling volume are smoke particles or not. As known to those of skill in the art, light emitters such as light-emitting diodes (LEDs) and lasers that emit at particular wavelengths may be produced by, e.g., selection and/or adjustment of the band gap and/or lasing cavity size of a semiconductor-based light emitter.

Figure 1A:
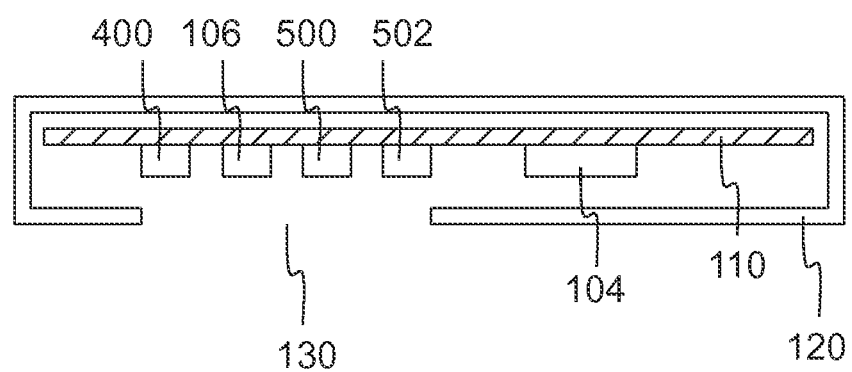
FIG. 1A is a cross-sectional diagram of a smoke detector with discrete light emitters emitting at different wavelengths, a discrete proximity sensor, and a discrete ambient-light sensor in accordance with various embodiments of the invention.

FIG. 1A depicts a smoke detector in accordance with various embodiments of the invention. As shown, the smoke detector includes a red light emitter 500, a blue light emitter 502, a proximity sensor 106, and an ambient-light sensor 400 that are mounted onto a circuit board 110 (or otherwise mounted within a surrounding housing 120). An evaluation circuit 104 may also be mounted on the circuit board 110. All of these components are typically disposed at least partially inside a smoke-detector housing 120, which includes or consists essentially of one or more rigid materials (e.g., metal, plastic, etc.). In various embodiments of the invention, the housing 120 has a single opening 130 that is situated over the red light emitter 500, the blue light emitter 502, the proximity sensor 106, and the ambient-light sensor 400. (As shown in FIG. 1A, the opening 130 is "over" all of these components in the sense that it is disposed opposite the circuit board 110 on which these components are mounted; in embodiments in which the smoke detector is mounted, e.g., on a ceiling, the opening 130 would be disposed "under" or "beneath" all of these components as pictured.) A window may be disposed within (and at least partially close) the opening 130. The window may include or consist essentially of, e.g., plastic and/or glass, and is generally at least partially transparent to light emitted by the red light emitter 500, light emitted by the blue light emitter 502, and ambient light. The housing 120 may also have multiple openings, with each opening situated over at least one component, and may have windows disposed within (and at least partially closing) one or more of the openings. In various embodiments of the invention, one or more of the components are connected to the circuit board 110 or another platform within the housing 120 but partially protrude outside of the housing 120, e.g., through the opening 130.

The red light emitter 500 and blue light emitter 502 emit at substantially different wavelengths. In various embodiments of the present invention, the red light emitter 500 emits red and/or infrared light, and the blue light emitter 502 emits blue, violet, and/or ultraviolet light. Generally, the blue light emitter 502 emits light of a shorter wavelength than light emitted by red light emitter 500; thus, the terms "blue light emitter" and "red light emitter" are utilized herein for convenience and to connote that one light emitter emits light of a shorter wavelength, rather than implying any particular emission wavelength from any particular light emitter. The blue light emitter 502 may emit light of a wavelength less than approximately 500 nm, and the red light emitter 500 may emit light of a wavelength greater than approximately 500 nm. In various embodiments of the invention, more than two light emitters may be utilized in the smoke detector, each with a substantially different wavelength from the other light emitters. In various embodiments of the present invention, a separate light detector may be utilized for each light emitter in the smoke detector. In various embodiments of the present invention, a broad spectrum of light may be emitted from the smoke detector by a single light emitter, and multiple different light detectors, each with a sensitivity to a different wavelength or range of wavelengths, may be utilized. For example, a first light detector may be more sensitive to red and/or infrared light, and a second light detector may be more sensitive to blue, violet, and/or ultraviolet light. In another example, the first light detector may be sensitive to both visible and infrared light, and the second light detector may be sensitive to only visible light. The single broadband emitter typically emits light over a wide range of wavelengths, and may include or consist essentially of one or more white LEDs (i.e., LEDs that emit white light or mixed light that closely approximates white light). Multiple different light emitters with different emission wavelengths may also be used in conjunction with the multiple light detectors. As known to those of skill in the art, light detectors such as photodetectors that are sensitive to light of particular wavelengths may be produced by, e.g., selection and/or adjustment of the band gap of a semiconductor-based light detector.

At least one light detector may be part of and may be embedded in the proximity sensor 106. The proximity sensor 106 may also control the operation of the red light emitter 500 and blue light emitter 502, which may be components separate and discrete from proximity sensor 106. An exemplary proximity sensor 106 in this embodiment is the Silicon Laboratories Si114x Proximity/Ambient Light Sensor, available from Silicon Laboratories Inc. of Austin, Tex. At least one of the red light emitter 500 and blue light emitter 502 may also be embedded in the proximity sensor 106. An exemplary proximity sensor 106 in this embodiment is the Vishay Intertechnology VCNL4000 Fully Integrated Proximity and Ambient Light Sensor, available from Vishay Intertechnology, Inc. of Malvern, Pa. If not embedded in the proximity sensor 106, the red light emitter 500 and blue light emitter 502 may be externally driven by the proximity sensor 106. At least one light detector is a part of and may be embedded in the ambient-light sensor 400. The light detector in the ambient-light sensor 400 is generally sensitive to visible light, but it may also be sensitive to ultraviolet and/or infrared light. A light detector includes or consists essentially of one or more devices that register the presence of and/or measure a property the light illuminating the device(s). For example, the light detector may produce charge (i.e., an electronic signal) when exposed to light. Exemplary light detectors include photodiodes, photodetectors, photoconductors, and/or photocapacitors. Alternative embodiments of the invention use a discrete light emitter and light detector in place of the proximity sensor without altering the functionality of the smoke detector. Other alternative embodiments of the invention use a discrete light detector in place of the ambient-light sensor without altering the functionality of the smoke detector.

Figure 1B:
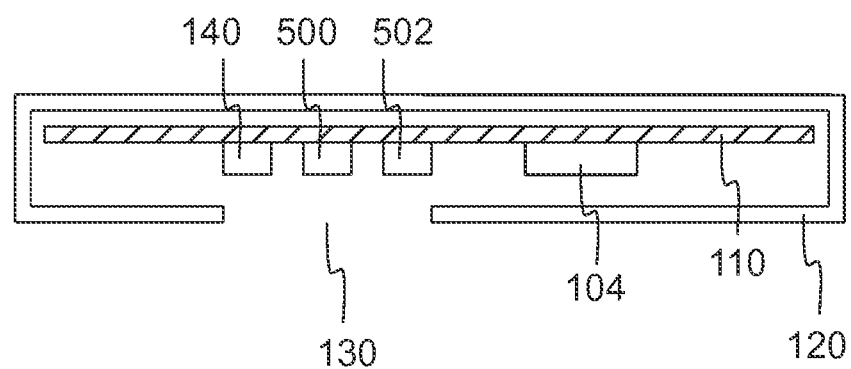
FIG. 1B is a cross-sectional diagram of a smoke detector with discrete light emitters emitting at different wavelengths and a proximity sensor featuring an embedded ambient-light sensor in accordance with various embodiments of the invention.

As shown in FIG. 1B, in a preferred embodiment of the present invention, the ambient-light sensor 400 is part of and even embedded within the proximity sensor 106 to form an integrated proximity/ambient-light sensor 140. In the integrated proximity/ambient-light sensor 140, the proximity sensor control circuitry is typically separate from the ambient-light sensor control circuitry, but the proximity sensor and ambient-light sensor may use at least one common light detector. At least one of the red light emitter 500 and blue light emitter 502 may also be part of and even embedded in the integrated proximity/ambient-light sensor 140.

Figure 1C:
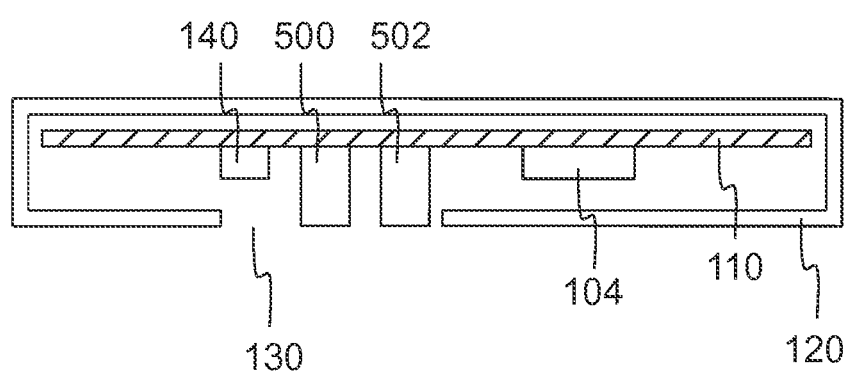
FIG. 1C is a cross-sectional diagram of a smoke detector with discrete light emitters emitting at different wavelengths, whereupon the light emitters are essentially flush with the smoke detector housing, and a proximity sensor featuring an embedded ambient-light sensor in accordance with various embodiments of the invention.
Figure 1D:
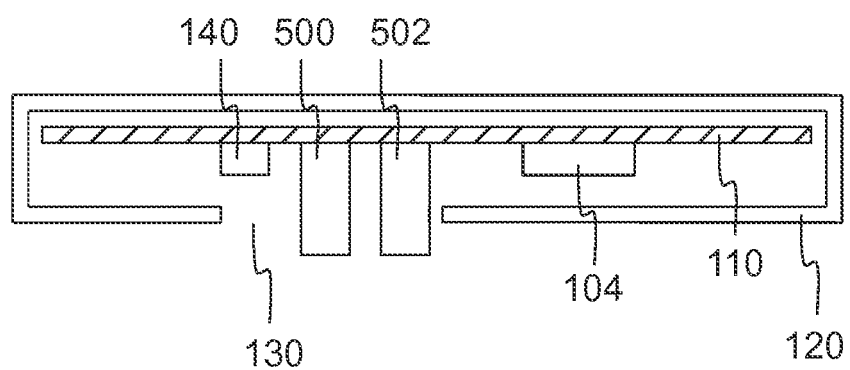
FIG. 1D is a cross-sectional diagram of a smoke detector with discrete light emitters emitting at different wavelengths, whereupon the light emitters partially protrude from the smoke detector housing, and a proximity sensor featuring an embedded ambient-light sensor in accordance with various embodiments of the invention.

To allow the maximum amount of light emitted by the red light emitter 500 and blue light emitter 502 to reach the external sampling volume, it may be advantageous to position the light emitters such that less light is blocked by the housing 120, especially if the width of the opening 130 is comparable or less than the width of the emitted light. As shown in one embodiment in FIG. 1C, leading portions of the red light emitter 500 and blue light emitter 502 are essentially flush with the housing 120. As shown in another embodiment in FIG. 1D, the red light emitter 500 and blue light emitter 502 partially protrude out of the housing 120 through the opening 130. In these two embodiments, the red light emitter 500 and blue light emitter 502 may be mounted onto circuit board 110 or mounted onto a separate circuit board that is otherwise electrically connected to circuit board 110, for example, onto a daughterboard or flex circuit board.

Figure 2A:
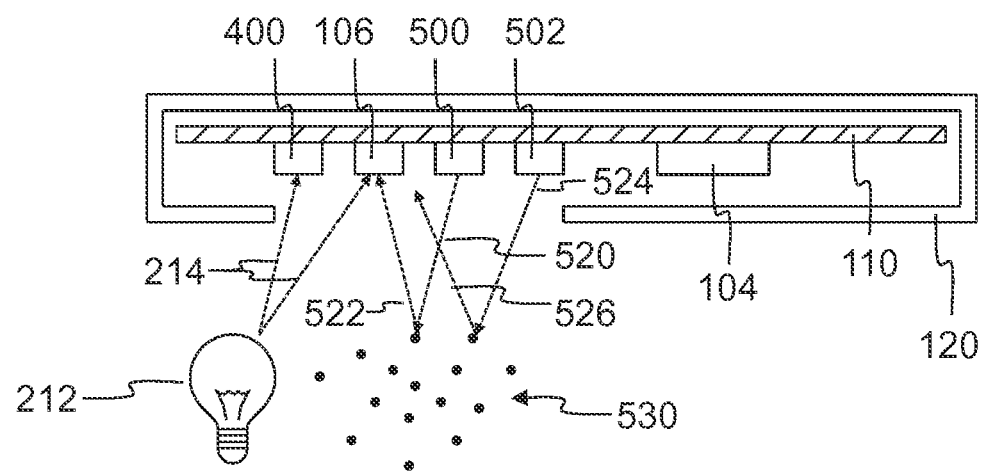
FIG. 2A illustrates signal generation from smoke located in a sampling volume and ambient light from an ambient light source in accordance with various embodiments of the invention.

Electronic signals are generated when light is collected (or "sensed" or "detected") by the light detectors embedded in the proximity sensor 106, integrated proximity/ambient-light sensor 140, and ambient-light sensor 400. As shown in FIG. 2A, at least three signals may be generated when airborne particles 530 are present in the external sampling volume. An emitted beam 520 (which may include or consist essentially of, e.g., red or infrared light) from red light emitter 500 may pass through the opening 130 in the housing 120 and be scattered by airborne particles 530, generating a red scattered beam 522. At least some of the red scattered beam 522 may pass back through the opening 130 in housing 120 and be collected by the proximity sensor 106, producing a "red signal." An emitted beam 524 (which may include or consist essentially of, e.g., blue, violet, and/or ultraviolet light) from blue light emitter 502 may also pass through the opening 130 in housing 120 and be scattered by the airborne particles 530. At least some of the blue scattered beam 526 may pass back through the opening 130 in housing 120 and be collected by the proximity sensor 106, generating a "blue signal." An ambient light beam 214 from an ambient light source 212 may also pass through the opening 130 in housing 120 and be collected by the ambient-light sensor 400, generating an "ambient signal." Example ambient light sources include sunlight or light from incandescent, fluorescent, halogen, or LED light bulbs. The ambient light beam 214, after passing through the opening 130 in housing 120, may also be partially collected by the proximity sensor 106, and may thus contribute to the red signal and/or the blue signal.

Signals may also be generated when an obstruction is present in the external sampling volume. The obstruction may be any object other than smoke particles or nuisance particles, such as but not limited to a person, furniture, or a cleaning instrument.

In various embodiments of the invention, the light emitted by the red light emitter 500 and blue light emitter 502 may be separately pulsed to temporally distinguish the signals from each other and to reduce power consumption. For example, only one of the light emitters 500, 502 may be emitting light at any particular time. As another example, the blue light emitter 502 may be pulsed less frequently than the red light emitter 500 to be more visually inconspicuous to a person near the smoke detector. Thus, the blue signal may be collected and/or processed less frequently than the red signal.

Figure 2B:
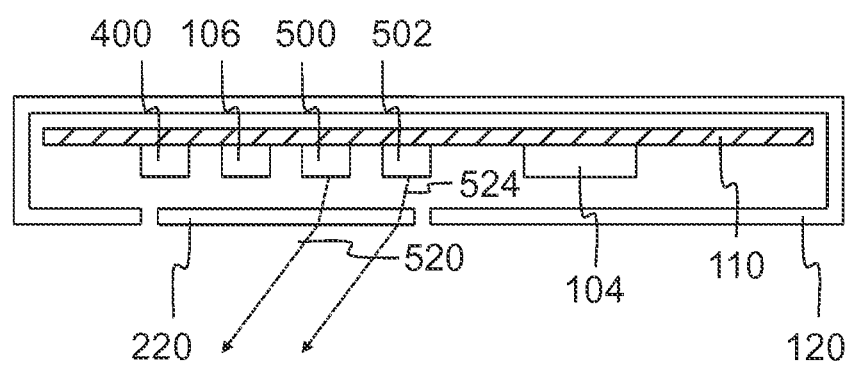
FIG. 2B is a cross-sectional diagram of a smoke detector with discrete light emitters emitting at different wavelengths, a discrete proximity sensor, a discrete ambient-light sensor, and an optical element in accordance with various embodiments of the invention.

As shown in FIG. 2B, an optical element 220 may be disposed in the housing 120. In general, the optical element 220 deflects the trajectories of at least a portion of the emitted beam 520 from red light emitter 500 and at least a portion of the emitted beam 524 from blue light emitter 502. The optical element 220 may include or consist essentially of a refractive element, such as a lens, prism, or grating, or a reflective element, such as a mirror. Likewise, multiple optical elements may be used to deflect the trajectories of emitted beam 520 and emitted beam 524. Deflecting the trajectories of the emitted beams shifts the position and/or size of the sampling volume(s) defined by the emitted beams such that it is more closely overhead (i.e., disposed more directly over) the proximity sensor 106. (Specifically, the sampling volume(s) may be positioned such that an imaginary line originating from the proximity sensor 106 and perpendicular to the plane of the circuit board 110 and/or the housing 120 passes through the sampling volume(s).) This increases the red and blue signals collected by the proximity sensor 106 compared to embodiments in which the sampling volume is farther away from the proximity sensor 106, thereby increasing the sensitivity of the smoke detector to particles inside the sampling volume. In some embodiments, the emitted beams are focused by one or more optical elements 220, thereby decreasing the size of the sampling volume; the focal point may be disposed directly over the proximity sensor 106 in order to increase the strength of the red and blue signals.

Figure 2C:
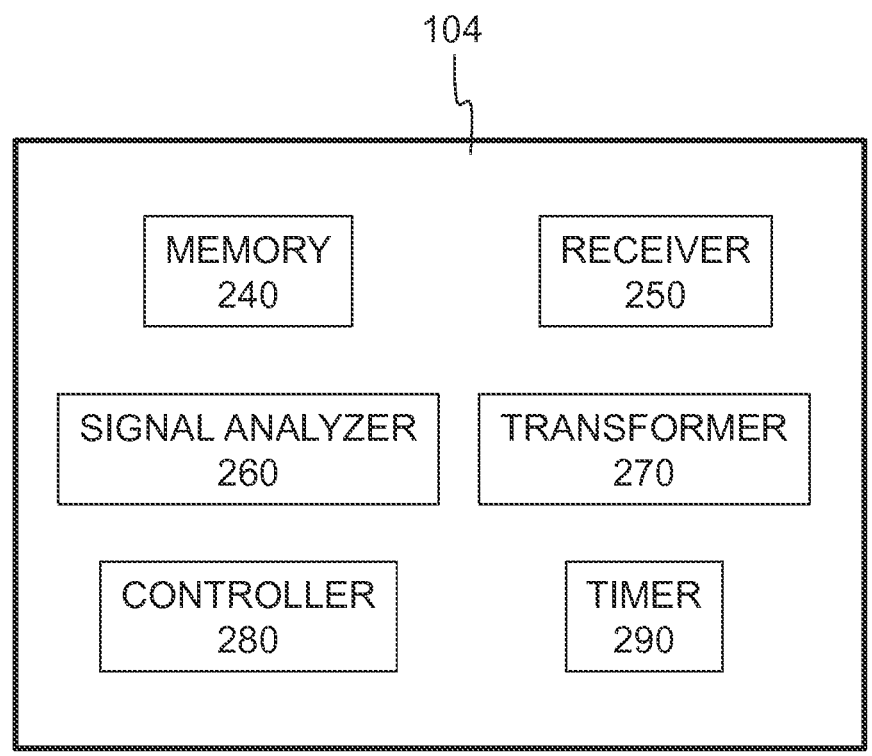
FIG. 2C is a block diagram of an evaluation circuit in accordance with various embodiments of the invention.

At least portions of the signals collected by the light detectors in the proximity sensor 106 and ambient-light sensor 400 are typically transmitted to the evaluation circuit 104, which analyzes the signals to determine whether smoke particles, nuisance particles, or an obstruction is present in the sampling volume. FIG. 2C schematically depicts various components of the evaluation circuit 104, which may include (but not be limited to) a memory 240, a receiver 250, a signal analyzer 260, a transformer 270, a controller 280, and/or a timer 290. The memory 240 may store pre-determined values (e.g., thresholds) utilized in sensing and/or control operations, and/or may store various signal values during and/or after they are sensed, corrected, and/or transformed (e.g., smoothed). At least a portion of memory 240 may be volatile, and at least a portion of memory 240 may be non-volatile. The receiver 250 may receive signals from other components of the smoke detector (e.g., light detectors and other sensors) and route the signals to other portions of the evaluation circuit 104. The signal analyzer 260 may compare received (and/or corrected and/or transformed) signals to various pre-determined threshold levels and/or to previously received (and/or corrected and/or transformed) signals to determine if smoke particles, nuisance particles, or an obstruction is present. The transformer (or "transform module" or "transformation module") 270 may transform received signals to, e.g., reduce or eliminate noise and/or compensate for drift. For example, the transformer 270 may implement smoothing (e.g., exponential smoothing and/or moving-average smoothing), filtering (e.g., high-pass, low-pass, and/or band-pass filtering), regression, and/or other numerical transformation techniques. The transformer 270 may also correct received signals based on, e.g., other received signals from one or more light detectors and/or ambient-light sensors, as detailed below. The controller 280 may control light emitters, light detectors, and/or other components of the smoke detector; for example, the controller 280 may control speakers that emit audible alarms and/or light sources in response to a sensed alarm condition or as part of a test sequence. The timer 290 may measure time elapsed during or since various sensed conditions and/or may be utilized to measure pre-determined delays utilized in various sensing or testing sequences.

The evaluation circuit 104 (and/or any or all of its components) may be a general-purpose microprocessor, but depending on implementation may alternatively be a microcontroller, peripheral integrated circuit element, a customer-specific integrated circuit (CSIC), an application-specific integrated circuit (ASIC), a logic circuit, a digital signal processor, a programmable logic device such as a field-programmable gate array (FPGA), a programmable logic device (PLD), a programmable logic array (PLA), an RFID processor, smart chip, or any other device or arrangement of devices that is capable of implementing the steps of the processes of embodiments of the invention. In a preferred embodiment, the evaluation circuit 104 is a microcontroller. The evaluation circuit 104 may be monolithically integrated with, and thus a portion of the same integrated-circuit chip as the proximity sensor 106 and/or ambient-light sensor 400, or evaluation circuit 104 may be disposed on a chip separate and discrete from the chip containing the proximity sensor 106 and/or ambient-light sensor 400 (and interconnected thereto by wired or wireless means). Moreover, at least some of the functions of evaluation circuit 104 may be implemented in software and/or as mixed hardware-software modules. Software programs implementing the functionality herein described may be written in any of a number of high level languages such as FORTRAN, PASCAL, JAVA, C, C++, C#, BASIC, various scripting languages, and/or HTML. Additionally, the software may be implemented in an assembly language directed to a microprocessor resident in evaluation circuit 104. The software may be embodied on an article of manufacture including, but not limited to, a floppy disk, a jump drive, a hard disk, an optical disk, a magnetic tape, a PROM, an EPROM, EEPROM, field-programmable gate array, CDROM, or DVDROM. Embodiments using hardware-software modules may be implemented using, for example, one or more FPGA, CPLD, or ASIC processors.

As mentioned above, the luminance of the ambient light beam 214 may partially contribute to the red signal and/or blue signal measured by the proximity sensor. When there is a change in the ambient light level, this may cause a change in the red and/or blue signal, which may cause a false alarm even though there are no particles or objects in the sampling volume. The change in ambient light level may occur nearly instantaneously, such when a room light is turned on or there is AC ripple in the luminance output of a light bulb, or the change in ambient light level may occur much more slowly, such as near dusk or dawn when the sun rises or sets.

Figure 3:
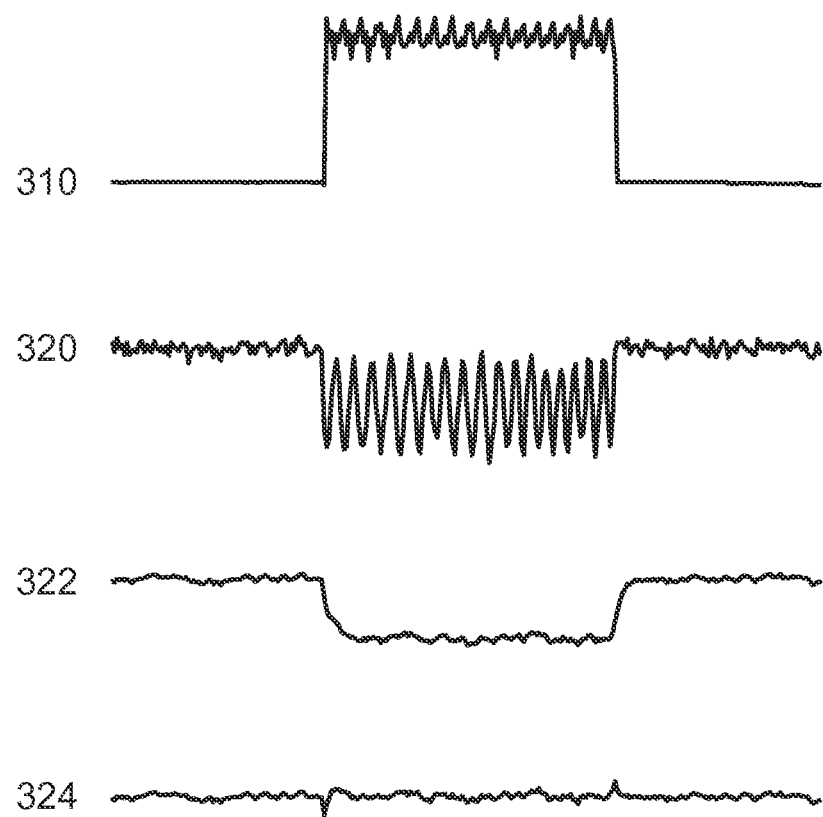
FIG. 3 displays an ambient light signal, an uncorrected proximity sensor signal, a partially corrected proximity sensor signal, and a corrected proximity sensor signal in accordance with various embodiments of the invention.

In preferred embodiments of the present invention, to compensate for changes in the ambient light level, the red signal and blue signal measured by the proximity sensor 106 are corrected by the evaluation circuit 104 based on the value of the ambient signal measured by the ambient-light sensor 400. FIG. 3 illustrates the application of ambient light correction in accordance with various embodiments of the invention. In the exemplary signals in FIG. 3, the room is initially dark (as perceived by the naked eye), then at a first time an incandescent light bulb is turned on, then at a second time the incandescent light bulb is turned off. At no time do particles or obstructions enter the sampling volume. In an exemplary temporal ambient light signal 310, three distinct regions are observed: a first region when the room is dark and the ambient light level is small and static, a second region when the incandescent light bulb is turned on and the ambient light level is elevated and dynamic, and a third region when the incandescent light bulb is turned off and the ambient light level is once again small and static. The sawtooth pattern in the second region is due to the AC ripple in the luminance output of the incandescent light bulb, which is absent when the light bulb is off. An exemplary temporal uncorrected red signal 320 is output by the proximity sensor 106 over the same time interval as the ambient light signal 310. In the first and third regions, the uncorrected red signal 320 is approximately static. In the second region, the uncorrected red signal 320 has a similar sawtooth pattern that temporally correlates with the ambient light signal 310. In various embodiments of the invention, the uncorrected red signal 320 undergoes a first correction to eliminate the sawtooth pattern. In the first correction, the proximity sensor 106 takes three measurements within a short time period, e.g., less than one millisecond: a first measurement when the red light emitter 500 is unilluminated, a second measurement when the red light emitter 500 is illuminated, and a third measurement when the red light emitter 500 is again unilluminated. The first and third measurements are averaged (e.g., an unweighted average or a weighted average weighting one of the measurements more than the other) and subtracted from the second measurement. In an alternative embodiment, measurements are taken at least as frequently as the Nyquist rate of the AC ripple and the amplitude of the ripple is fitted by the evaluation circuit 104 and substantially eliminated from the uncorrected red signal 320. The result after the first correction is a partially corrected red signal 322. By performing the three measurements over a time period (e.g., <1 ms) much shorter than the 120 Hz AC light ripple time period (~8.3 ms), the sawtooth pattern in the partially corrected red signal 322 is eliminated; however, there is still a residual offset in the second region. The magnitude of the offset is related to the luminance of the ambient light level. In some embodiments of the present invention, only one measurement when the red light emitter 500 is unilluminated is performed (either before or after the measurement when the red light emitter is illuminated), and/or utilized (i.e., without averaging) to correct the illuminated signal to produce the partially corrected red signal 322; however, embodiments utilizing multiple measurements when the light emitter is unilluminated may provide signals from which the presence of smoke and/or nuisance particles may be more accurately determined, particularly in environments with rapidly changing light levels and/or when light emitters emit noisy or highly oscillatory light. In various embodiments of the invention, the partially correlated red signal 322 undergoes a second correction based on the ambient signal measured by ambient-light sensor 400. In the second correction, the partially corrected red signal is adjusted by the ambient signal according to:

$$R_c = R + f(A,R),$$

where $R_c$ is the corrected red signal, R is the uncorrected (or partially corrected) red signal, and A is the ambient signal. The function $f(A,R)$ may be a linear or polynomial function of A only, R only, or both A and R. In a preferred embodiment, the function $f(A,R)$ is a linear function of A only taking the form $f(A)=mA$, where m is a constant scalar. The result after the second correction is a corrected red signal 324. The second correction decreases or substantially eliminates the residual offset in the second region. Although only the correction of the red signal was illustrated in this experiment, both the red signal and blue signal may be corrected using this technique. In some embodiments, the red and blue signal are both corrected based on the same one or more unilluminated measurements (i.e., measurements taken without emission of red or blue light).

If the luminance of the ambient light beam 214 onto the proximity sensor 106 and/or the ambient-light sensor 400 becomes very intense, such as when the sensors are directly illuminated by the sun or a very bright light bulb, either sensor may saturate, which prevents them from outputting signals and may even effectively halt the operation of the smoke detector. If either sensor becomes saturated or reaches a threshold signal near the saturation level (e.g., 90% of the saturation level), the evaluation circuit 104 may switch to a different light detector embedded in the proximity sensor 106 or ambient-light sensor 400 with a lower responsivity to avoid the saturation condition and ensure operation of the smoke detector even when directly exposed to very high ambient light levels. Alternatively, if either sensor becomes saturated or reaches a threshold signal near the saturation level, the evaluation circuit 104 may lower the gain of the light detector embedded in the proximity sensor 106 or ambient-light sensor 400 to avoid the saturation condition.

Figure 4:
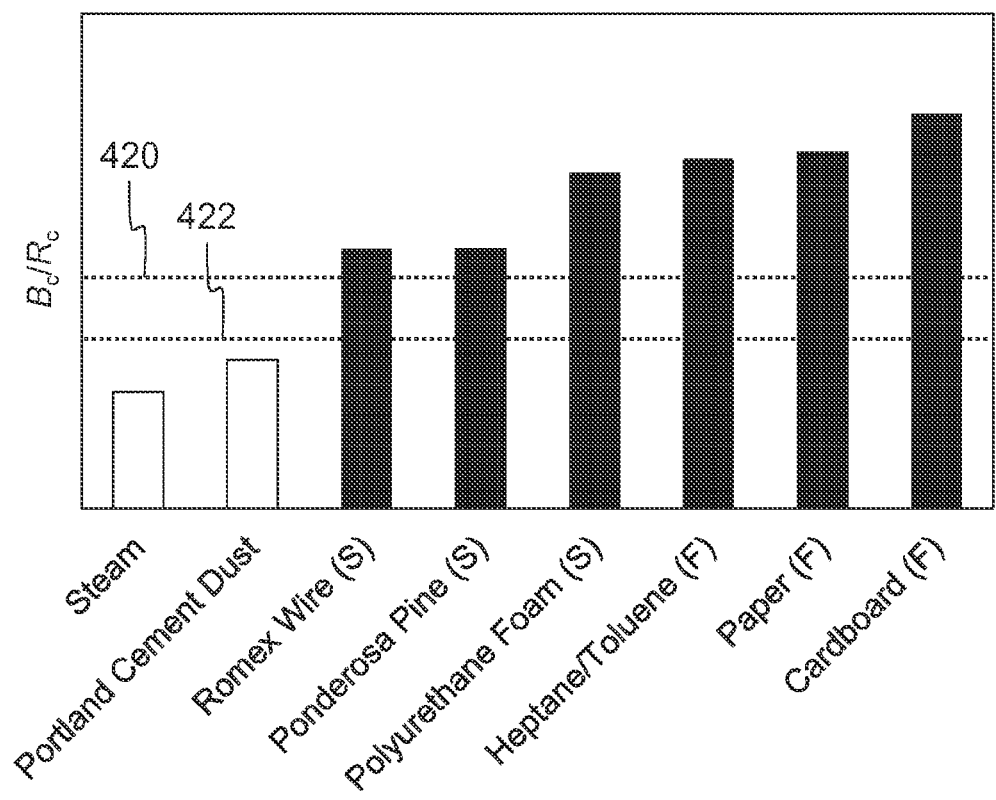
FIG. 4 displays the ratio of corrected proximity sensor signals of two different wavelengths for several nuisance and fire sources in accordance with various embodiments of the invention.

The corrected red and blue signals may be used to determine if particles inside the sampling volume are smoke particles or nuisance particles. As mentioned above, nuisance particles scatter red (and infrared) and blue (and violet and ultraviolet) light generally equally because these particles have diameters on the order of several microns, whereas smoke particles scatter blue light more strongly than red light because these particles have diameters of less than one micron. By taking the ratio or the difference between the corrected blue signal and corrected red signal of particles in the sampling volume, the evaluation circuit 104 may determine if the particles are smoke particles or nuisance particles. FIG. 4 shows the ratio of the corrected blue signal to the corrected red signal (designated $B_c/R_c$) of various sources in accordance with various embodiments of the present invention. In experimental trials, both nuisance sources (represented by white bars) and fire sources (represented by black bars) were tested. Fire sources are divided into smoldering fires (represented by the letter 'S') and flaming fires (represented by the letter 'F'). The corrected blue/red signal ratio of the nuisance sources is generally smaller than the corrected blue/red signal ratio of the fire sources. Also, the corrected blue/red signal ratio of the smoldering fire sources is generally smaller than the corrected blue/red signal ratio of the flaming fire sources. In an embodiment of the invention, if the corrected blue/red signal ratio is above a first ratio threshold 420, then the particles in the sampling volume are determined to be smoke particles. If the corrected blue/red signal ratio is below a second ratio threshold 422, then the particles in the sampling volume are determined to be nuisance particles. If the corrected blue/red signal ratio is in between the first ratio threshold 420 and second ratio threshold 422, then no determination on the particles is made and additional measurements may be taken. In some embodiments of the invention, the first and second ratio thresholds 420, 422 are substantially equal—i.e., only one ratio threshold is utilized to determine between smoke and nuisance particles.

To minimize the effects of noise and drift in a detected signal (e.g., the red signal, blue signal, or ambient signal), the evaluation circuit 104 may apply smoothing to the signal. In a preferred embodiment, the smoothing is an exponential smoothing. Specifically, for a current sensor reading x, the smoothed signal S is assigned the following value:

$$S := \alpha x + (1-\alpha)S,$$

where α is the smoothing factor. As implied by the use of the assignment operator (':=') in the above expression, the smoothed signal S may be updated without the use of another variable. The smoothing factor α is in the range of $0 < \alpha < 1$.

In various embodiments of the present invention, slowly varying and quickly varying signals may be distinguished by calculating two smoothed signals and taking the difference. The first smoothed signal has a larger smoothing factor α, typically in the range of $0.01 < \alpha < 1$. It may track signals that change over the course of seconds or minutes without significant lag. The second smoothed signal has a smaller smoothing factor α, typically in the range of $0.0001 < \alpha < 0.01$. It may only track signals that change over the course of hours without significant lag. When there is a slowly varying drift in the signal, both the first and second smoothed signals may track the drift without significant lag. The differential signal in this case will typically be approximately zero. In contrast, the insertion of smoke particles, nuisance particles, or an obstruction in the sample volume results in a more quickly varying change in the signal. The first smoothed signal may track the change without significant lag but the second smoothed signal generally will not. The differential signal in this case will typically have a positive value that may exceed an alarm threshold value.

If the second smoothed signal is ever larger than the first smoothed signal, which may occur if there is a decrease in the detected signal, then the second smoothed signal is assigned the value of the first smoothed signal. This ensures the differential signal will always be positive when there is an increase in the detected signal, so that any potential alarm condition will not be delayed or undetected.

The differential signal, based on either the corrected red signal or corrected blue signal (and hereafter referred to as the signal), may be used to determine if an object inside the sampling volume is particles or an obstruction. This may be accomplished by establishing two thresholds, an obstruction threshold and a smoke threshold. A solid object has a much larger cross-sectional area than smoke particles; therefore, the object will generally produce a distinctly stronger signal than the smoke particles, even for very high smoke obscurations (or densities) of greater than 40%/ft. Thus, the obstruction threshold is preferably set higher than the signal generated when the smoke obscuration is approximately 40%/ft. If the signal exceeds the obstruction threshold for a pre-determined amount of time, an obstruction alarm (i.e., an audible tone or visible light on the smoke detector itself or on an external notification device) may be activated. The pre-determined delay eliminates unwanted (or "false") alarms from fleeting events such as an insect passing through the external sampling volume.

The smoke threshold is typically set lower than the obstruction threshold. The smoke threshold may correspond to the signal generated when the smoke obscuration exceeds approximately 0.5%/ft but typically not greater than approximately 4%/ft in the external sampling volume. If the signal exceeds the smoke threshold for a pre-determined amount of time, a smoke alarm (i.e., an audible tone or visible light on the smoke detector itself or on an external notification device) may be activated. The smoke alarm may be different from the obstruction alarm in tone, duration, volume, intensity, color, and/or frequency.

Manual system testing of the smoke detector may be performed by inserting an object, such as a hand or broom handle, into the external sampling volume for a pre-determined amount of time (e.g., a minimum duration of 2-20 seconds) to intentionally increase the signal and activate either the obstruction alarm or smoke alarm. If an alarm is already activated, an object may be inserted into the external sampling volume for a pre-determined amount of time to temporarily or permanently (at least for the currently sensed condition and/or until the smoke detector is reset) silence the alarm.

Figure 5:
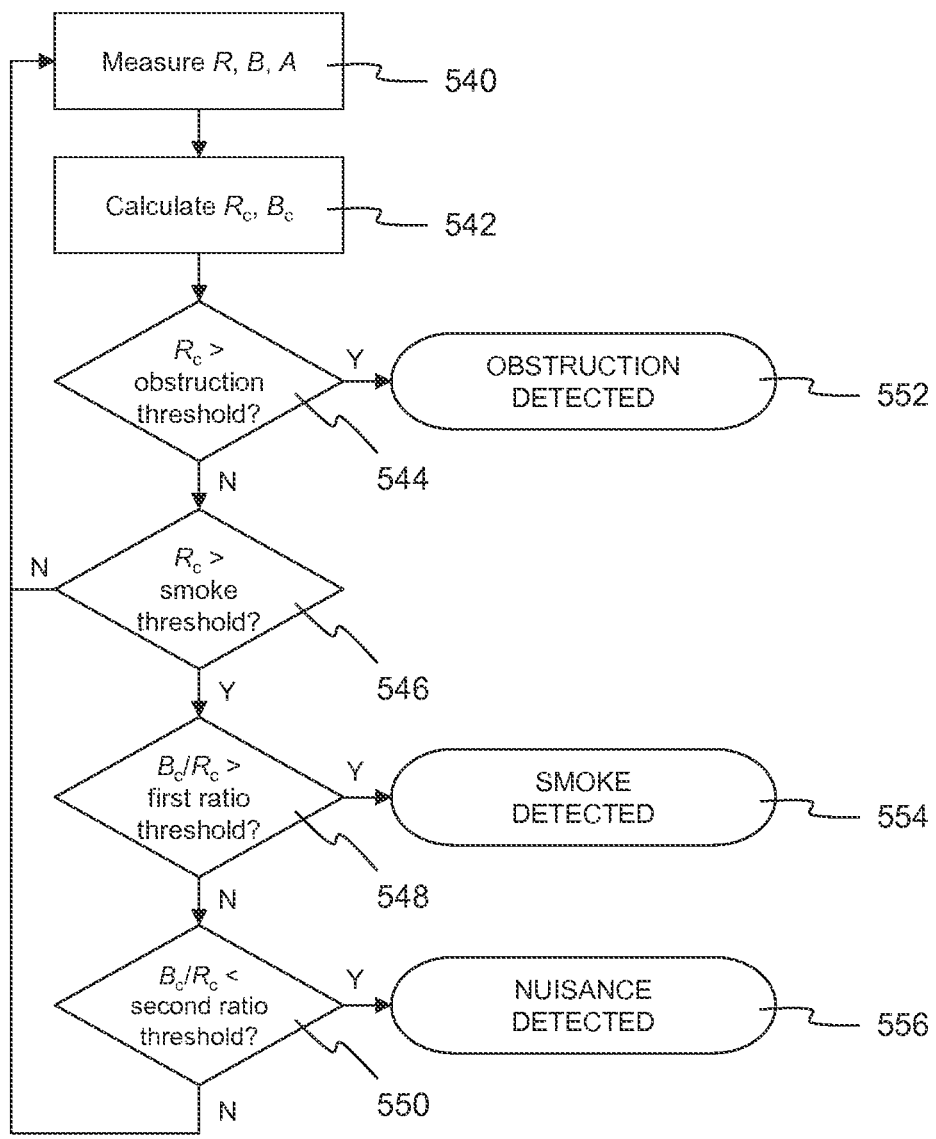
FIG. 5 is a flow chart depicting a method to distinguish smoke particles, nuisance particles, and obstructions in accordance with various embodiments of the invention.

In various embodiments above, the evaluation circuit 104 analyzes the temporal pattern of detected signal(s) to determine whether there are smoke particles, nuisance particles, or an obstruction present in the sampling volume of the smoke detector, and take the appropriate action of whether to activate a smoke alarm, obstruction alarm, or no alarm. Another exemplary technique of determining which condition is present, if any, is illustrated in FIG. 5. This is an exemplary standby sequence that may be followed by a smoke detector when no detected or calculated signals have exceeded any threshold values and that may be executed by evaluation circuit 104 (e.g., as depicted in FIG. 2B).

In a process step 540, the uncorrected red signal R, uncorrected blue signal B, and ambient signal A are measured. In an embodiment, any of the signals may be the average of multiple measurements. In another embodiment, signal smoothing may be applied to any or all of these signals. In another embodiment, the measurements of all signals occur in less than 100 milliseconds, and preferably in less than 1 millisecond. In another embodiment, a short delay (for example of approximately 0.1-10 seconds) may be inserted before the measurement to reduce power consumption of the smoke detector. Such reduction in power consumption may be important when the smoke detector is powered by a battery to increase battery lifetime. In another embodiment, the uncorrected blue signal may be measured less frequently than the uncorrected red signal.

In a process step 542, the corrected red signal $R_c$ and corrected blue signal $B_c$ are calculated based on the uncorrected red signal R, uncorrected blue signal B, and ambient signal A. In an embodiment, $R_c = R + f(A,R)$ and $B_c = B + f(A,B)$, as described above. In a preferred embodiment, $R_c = R + mA$ and $B_c = B + nA$, where m and n are scalar constants.

In a decision step 544, if $R_c$ is greater than a specified obstruction threshold, then an obstruction is present in the sampling volume and an obstruction detection sequence 552 may be activated. When smoke particles or nuisance particles are present in the external sampling volume, even with a very high obscuration density, the amount of scattered light from the particles is typically still less than the amount of reflected light from a physical obstruction in the external sampling volume. This is particularly true because the particles typically would not build up to a high obscuration density within one measurement cycle of the standby sequence, whereas a physical obstruction may be inserted into the external sampling volume within one measurement cycle, leading to a large increase in $R_c$ between cycles. The obstruction threshold is preferably set at a level that cannot reasonably be reached by the buildup of smoke within one measurement cycle. In an alternative embodiment, $B_c$ is used as the determining variable instead of $R_c$.

In a decision step 546, if $R_c$ is greater than a specified smoke threshold (and less than the obstruction threshold), then it indicates that something other than an obstruction is present in the sampling volume. If the condition is not true, then process step 540 is repeated. The smoke threshold is typically less than the obstruction threshold. As with almost any electrical signal, the signal will typically contain noise, which may be characterized as a random signal added to the "true" signal. The smoke threshold is preferably set at a level that cannot reasonably be reached through the addition of noise. In a preferred embodiment, the smoke threshold may correspond to the signal generated when the smoke obscuration exceeds approximately 0.5%/ft but typically not greater than approximately 4%/ft in the external sampling volume. In an alternative embodiment, $B_c$ is used as the determining variable instead of $R_c$.

In a decision step 548, if the ratio $B_c/R_c$ is greater than a specified first ratio threshold (e.g., first ratio threshold 420), then smoke particles are present in the sampling volume and a smoke detection sequence 554 may be activated. The first ratio threshold is typically less than the ratios measured for smoke particles generated by flaming and smoldering fires. The first ratio threshold is typically greater than the second ratio threshold described below.

In a decision step 550, if the ratio $B_c/R_c$ is less than a specified second ratio threshold (e.g., second ratio threshold 422), then nuisance particles are present in the sampling volume and a nuisance detection sequence 556 may be activated. If the condition is not true, then process step 540 is repeated. The second ratio threshold is typically less than the first ratio threshold. The second ratio threshold is typically greater than the ratios measured for nuisance particles. In an embodiment, the first ratio threshold and second ratio threshold may be approximately equal.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of smoke detection utilizing a smoke detector comprising (a) a housing, (b) one or more light emitters, and (c) one or more light detectors, the method comprising:
    acquiring a measurement of light including a first wavelength from a first sampling volume while emitting light of approximately the first wavelength with at least one said light emitter;
    acquiring a measurement of light including a second wavelength from a second sampling volume while emitting light of approximately the second wavelength with at least one said light emitter, the second wavelength being longer than the first wavelength;
    detecting an ambient light level outside of the housing;
    correcting the measurement of light including the first wavelength based at least in part on the detected ambient light level, thereby producing a corrected first-wavelength measurement;
    correcting the measurement of light including the second wavelength based at least in part on the detected ambient light level, thereby producing a corrected second-wavelength measurement; and
    determining the presence of smoke particles based on a ratio of the corrected first-wavelength measurement to the corrected second-wavelength measurement.

2. The method of claim 1, wherein (i) producing the corrected first-wavelength measurement comprises adding to the measurement of light including the first wavelength a first offset based on a function of the detected ambient light level, and (ii) producing the corrected second-wavelength measurement comprises adding to the measurement of light including the first wavelength a second offset based on a function of the detected ambient light level.

3. The method of claim 2, wherein (i) the first offset is based on a linear or polynomial function of the detected ambient light level, and (ii) the second offset is based on a linear or polynomial function of the detected ambient light level.

4. The method of claim 1, wherein determining the presence of smoke particles comprises comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold.

5. The method of claim 4, wherein the first threshold corresponds to at least one of (i) a signal level larger than a signal level generated via smoke obscuration of approximately 0.5%/foot or (ii) a signal level smaller than a signal level generated via smoke obscuration of approximately 4%/foot.

6. The method of claim 1, further comprising determining, based on the ratio of the corrected first-wavelength measurement to the corrected second-wavelength measurement, the presence of nuisance particles having a larger average diameter than an average diameter of the smoke particles, wherein:
    determining the presence of smoke particles comprises comparing the ratio of the corrected first-wavelength measurement to the corrected second-wavelength measurement to a first threshold, smoke particles being determined to be present when the ratio of the corrected first-wavelength measurement to the corrected second-wavelength measurement is larger than the first threshold, and
    determining the presence of nuisance particles comprises comparing the ratio of the corrected first-wavelength measurement to the corrected second-wavelength measurement to a second threshold, nuisance particles being determined to be present when the ratio of the corrected first-wavelength measurement to the corrected second-wavelength measurement is smaller than the second threshold.

7. The method of claim 6, wherein the first threshold is approximately equal to the second threshold.

8. The method of claim 6, wherein the second threshold is lower than the first threshold.

9. The method of claim 1, wherein the one or more light emitters comprise a broadband light source emitting light over a range of wavelengths, the first and second wavelengths being within the range of wavelengths.

10. The method of claim 9, wherein the broadband light source comprises a white light-emitting diode.

11. The method of claim 1, wherein the one or more light emitters comprise a first light emitter emitting light at the first wavelength and a second light emitter, different from the first light emitter, emitting light at the second wavelength.

12. The method of claim 1, wherein the smoke detector comprises a proximity sensor, at least one said light detector being embedded within the proximity sensor.

13. The method of claim 12, wherein the smoke detector comprises an ambient light sensor discrete from the proximity sensor, at least one said light detector being embedded within the ambient light sensor.

14. The method of claim 1, wherein the first wavelength is between approximately 300 nm and approximately 480 nm.

15. The method of claim 1, wherein the second wavelength is between approximately 630 nm and approximately 1000 nm.

16. The method of claim 1, further comprising acquiring a first unilluminated measurement of light including the first wavelength and the second wavelength without emitting light of approximately the first wavelength or light of approximately the second wavelength from the one or more light emitters.

17. The method of claim 16, wherein (i) producing the corrected first-wavelength measurement comprises subtracting from the measurement of light including the first wavelength the first unilluminated measurement of light including the first wavelength and the second wavelength and (ii) producing the corrected second-wavelength measurement comprises subtracting from the measurement of light including the second wavelength the first unilluminated measurement of light including the first wavelength and the second wavelength.

18. The method of claim 16, wherein the first unilluminated measurement of light including the first wavelength and the second wavelength is acquired before the measurement of light including the first wavelength and the measurement of light including the second wavelength are acquired.

19. The method of claim 16, wherein at least one of the measurement of light including the first wavelength or the measurement of light including the second wavelength is acquired before the first unilluminated measurement of light including the first wavelength and the second wavelength is acquired.

20. The method of claim 16, wherein the first unilluminated measurement of light including the first wavelength and the second wavelength is acquired after the measurement of light including the first wavelength and the measurement of light including the second wavelength are acquired.

21. The method of claim 1, wherein the first sampling volume at least partially overlaps with the second sampling volume.

22. The method of claim 1, wherein the first and second sampling volumes are substantially the same.

23. The method of claim 1, wherein the first and second sampling volumes are disposed outside of the housing.

24. The method of claim 1, further comprising at least one of:
    altering a position of at least a portion of the first sampling volume by altering an emission trajectory of the emitted light of approximately the first wavelength; or
    altering a position of at least a portion of the second sampling volume by altering an emission trajectory of the emitted light of approximately the second wavelength.

* * * * *